(12) United States Patent
Arami et al.

(10) Patent No.: US 10,086,183 B2
(45) Date of Patent: Oct. 2, 2018

(54) APPLICATOR

(71) Applicant: HISAMITSU PHARMACEUTICAL CO., INC., Tosu-shi, Saga (JP)

(72) Inventors: Shunsuke Arami, Tsukuba (JP); Shinpei Nishimura, Tsukuba (JP); Seiji Tokumoto, Tsukuba (JP); Makoto Ogura, Tsukuba (JP)

(73) Assignee: HISAMITSU PHARMACEUTICAL CO., INC., Tosu-shi, Saga (JP)

( * ) Notice: Subject to any disclaimer, the term of this patent is extended or adjusted under 35 U.S.C. 154(b) by 142 days.

(21) Appl. No.: 15/032,709

(22) PCT Filed: Nov. 4, 2014

(86) PCT No.: PCT/JP2014/079272
§ 371 (c)(1),
(2) Date: Apr. 28, 2016

(87) PCT Pub. No.: WO2015/068702
PCT Pub. Date: May 14, 2015

(65) Prior Publication Data
US 2016/0263363 A1 Sep. 15, 2016

(30) Foreign Application Priority Data
Nov. 5, 2013 (JP) .................................. 2013-229691

(51) Int. Cl.
*A61M 37/00* (2006.01)

(52) U.S. Cl.
CPC . *A61M 37/0015* (2013.01); *A61M 2037/0023* (2013.01); *A61M 2037/0046* (2013.01); *A61M 2037/0061* (2013.01)

(58) Field of Classification Search
CPC ...... A61M 37/0015; A61M 2037/0061; A61M 2037/0023; A61M 2037/0046
See application file for complete search history.

(56) References Cited

U.S. PATENT DOCUMENTS

| 6,334,856 B1 | 1/2002 | Allen et al. |
| 2002/0123675 A1 | 9/2002 | Trautman et al. |

(Continued)

FOREIGN PATENT DOCUMENTS

| AU | 2012201016 A1 | 3/2012 |
| CN | 1479589 A | 3/2004 |

(Continued)

OTHER PUBLICATIONS

United States of America Non-Final Office Action dated Aug. 11, 2017, corresponding to U.S. Appl. No. 14/654,029.

(Continued)

*Primary Examiner* — Lauren P Farrar
(74) *Attorney, Agent, or Firm* — Nath Goldberg Meyer; Joshua Goldberg; Tanya Harkins

(57) ABSTRACT

An applicator is configured to transfer an active ingredient into a body through skin by a puncture in the skin with microneedles. The applicator includes a piston plate that is provided with a first protrusion part and second protrusion parts on a lower surface side of a main body of the piston plate. The microneedles are provided on a surface of the first protrusion part. The second protrusion parts are provided in a periphery of the first protrusion part while spaced apart from the first protrusion part.

8 Claims, 42 Drawing Sheets

(56) References Cited

U.S. PATENT DOCUMENTS

| | | |
|---|---|---|
| 2008/0039805 A1 | 2/2008 | Frederickson et al. |
| 2008/0156594 A1 | 7/2008 | Kobayashi |
| 2009/0198189 A1* | 8/2009 | Simons ............ A61M 37/0015 604/173 |
| 2010/0222743 A1 | 9/2010 | Frederickson et al. |
| 2011/0275994 A1 | 11/2011 | Iwase et al. |
| 2011/0276027 A1 | 11/2011 | Trautman et al. |
| 2012/0010529 A1 | 1/2012 | Chickering, III et al. |
| 2012/0130207 A1* | 5/2012 | O'dea ............... A61M 37/0015 600/309 |
| 2014/0039458 A1 | 2/2014 | Constantineau et al. |
| 2015/0314117 A1 | 11/2015 | Arami et al. |

FOREIGN PATENT DOCUMENTS

| | | |
|---|---|---|
| CN | 101513550 A | 8/2009 |
| CN | 102753234 A | 10/2012 |
| EP | 2399643 A1 | 12/2011 |
| JP | 2001525231 A | 12/2001 |
| JP | 2004510534 A | 4/2004 |
| JP | 2006500973 A | 1/2006 |
| JP | 2006276200 A | 10/2006 |
| JP | 2007516781 A | 6/2007 |
| JP | 2008535587 A | 9/2008 |
| JP | 2010211890 A | 9/2010 |
| JP | 4659332 B2 | 3/2011 |
| JP | 2012100783 A | 5/2012 |
| KR | 101111144 B1 | 2/2012 |
| TW | 201231109 A | 8/2012 |
| WO | 0009184 A1 | 2/2000 |
| WO | 2006103727 A1 | 10/2006 |
| WO | 2006105272 A2 | 10/2006 |
| WO | 2007124411 A1 | 11/2007 |
| WO | 2009107806 A2 | 9/2009 |
| WO | 2011075105 A1 | 6/2011 |
| WO | 2011084951 A2 | 7/2011 |
| WO | 2012046816 A1 | 4/2012 |
| WO | 2014097837 A1 | 6/2014 |
| WO | 2013015136 A1 | 2/2015 |
| WO | 2013051568 A1 | 3/2015 |

OTHER PUBLICATIONS

European Search Report dated Nov. 21, 2016 corresponding to application No. 13864780.5-1501.
Taiwanese Office Action dated Jul. 14, 2017 corresponding to application No. 102145132.
International Search Report dated Mar. 4, 2014 corresponding to International application No. PCT/JP2013/081944.
International Search Report dated Feb. 17, 2015 corresponding to International application No. PCT/JP2014/079272.
International Preliminary Report on Patentability dated Jul. 2, 2015 corresponding to International application No. PCT/JP2013/081944.
International Preliminary Report on Patentability dated May 19, 2016 corresponding to International application No. PCT/JP2014/079272.
Extended European Search Report dated Sep. 27, 2017 corresponding to application No. 14859702.4-1501.
International search report dated Nov. 22, 2016 for application PCT/JP2016/074221 with English abstract.
Office action dated Jan. 24, 2017 for corresponding CN application 201380071668.9.
Notice of Allowance dated Sep. 12, 2017 corresponding to Japanese application No. 2015-546649.

* cited by examiner

Fig.7
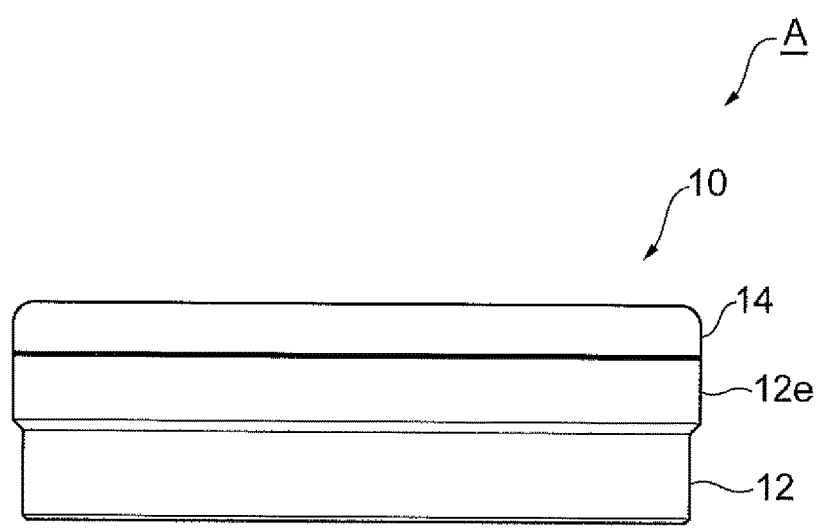
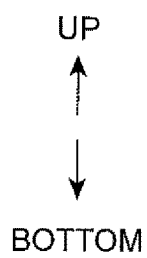

*Fig.8*
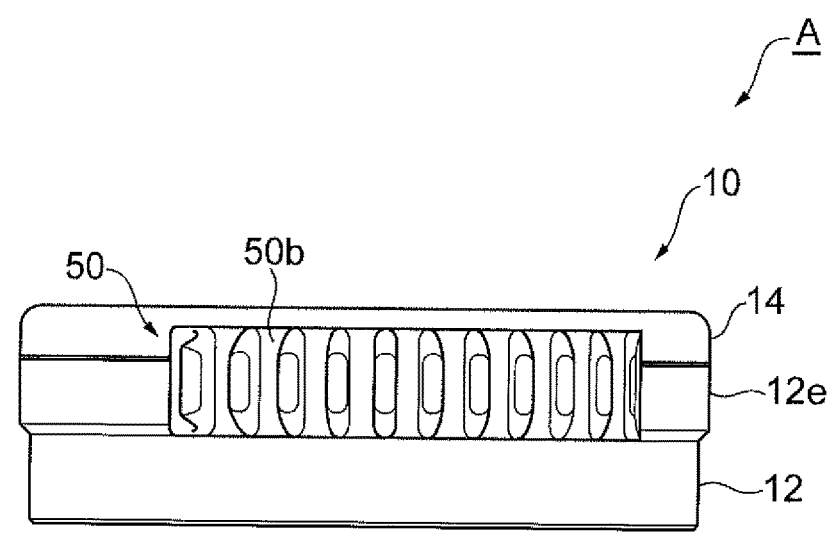
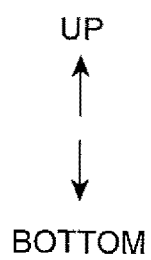

*Fig.27*
(a)
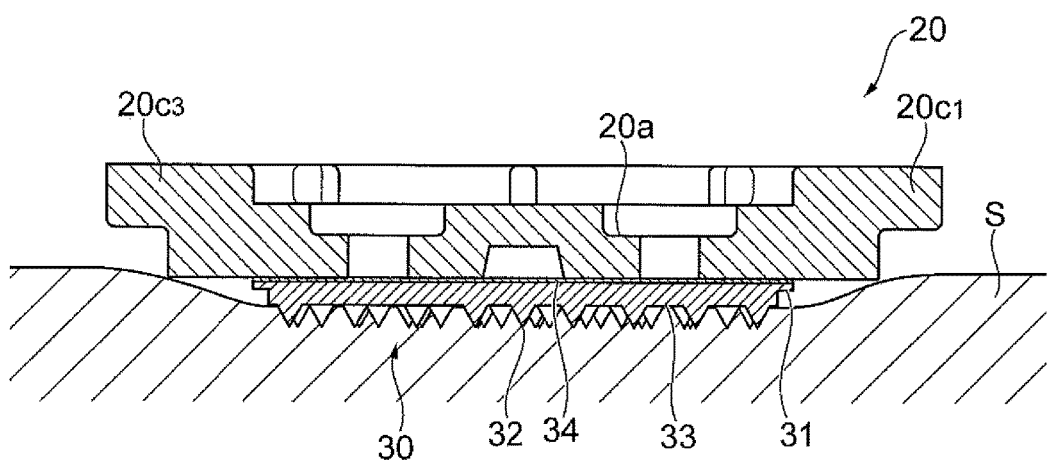
(b)
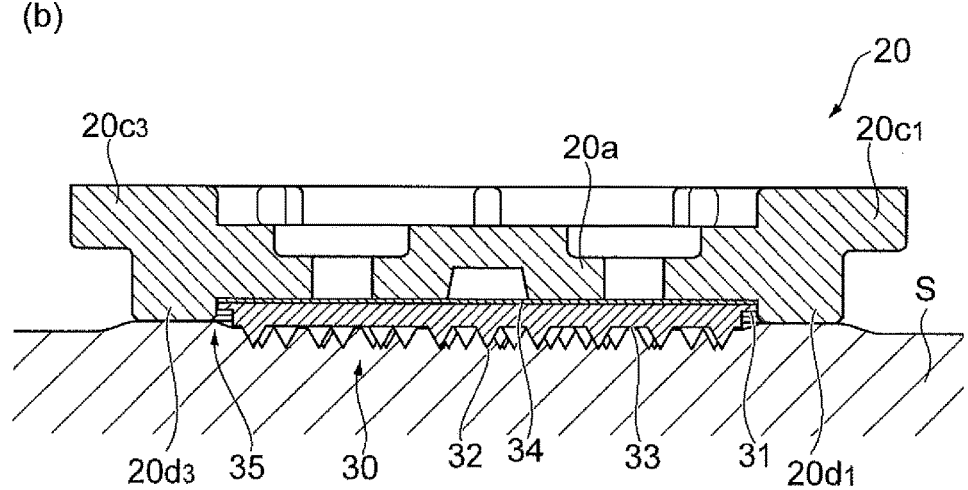

*Fig.28*
(a)
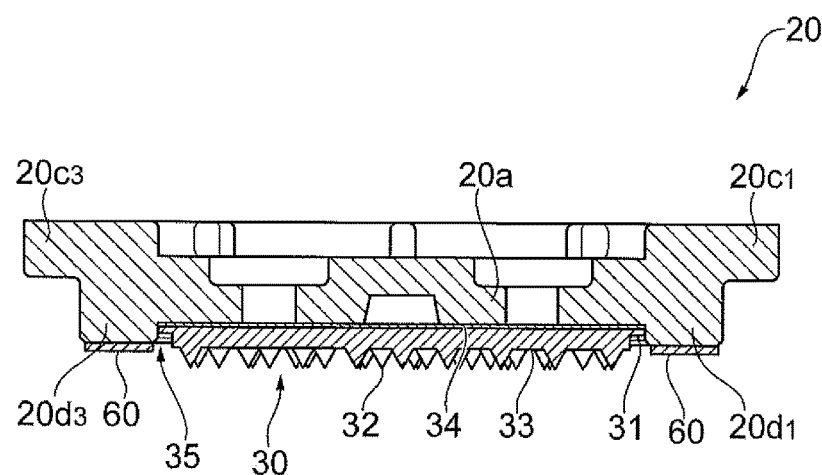
(b)
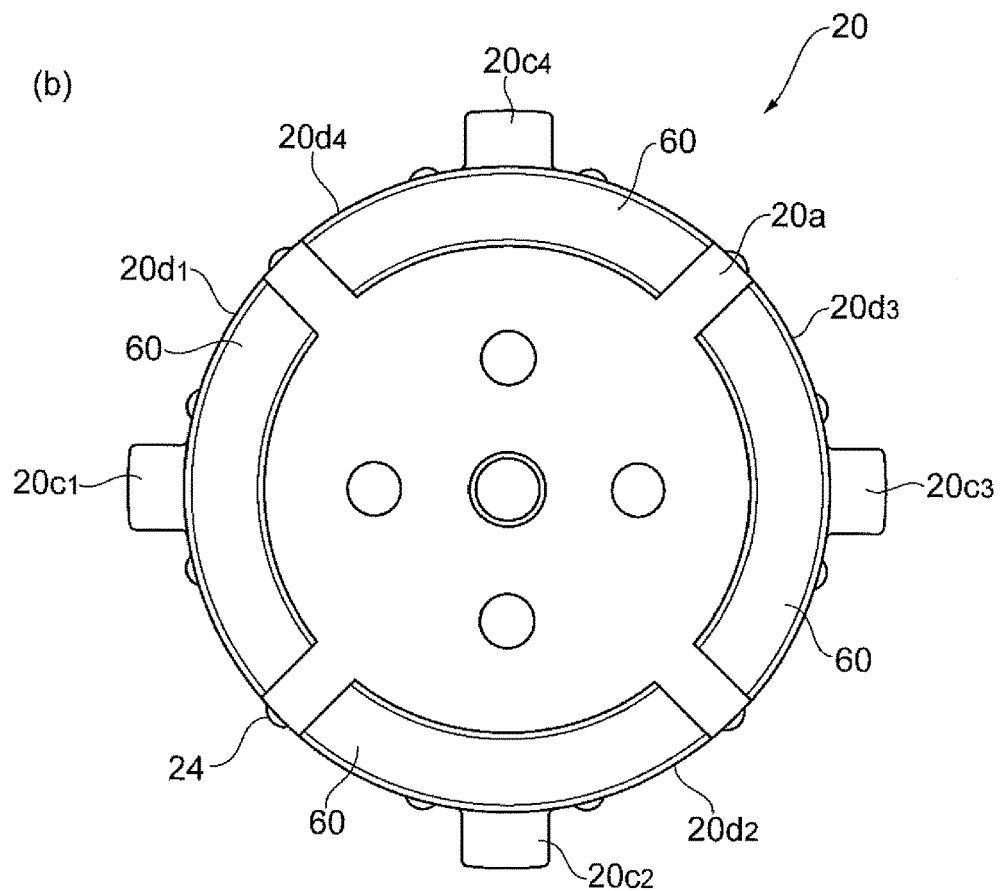

Fig.29
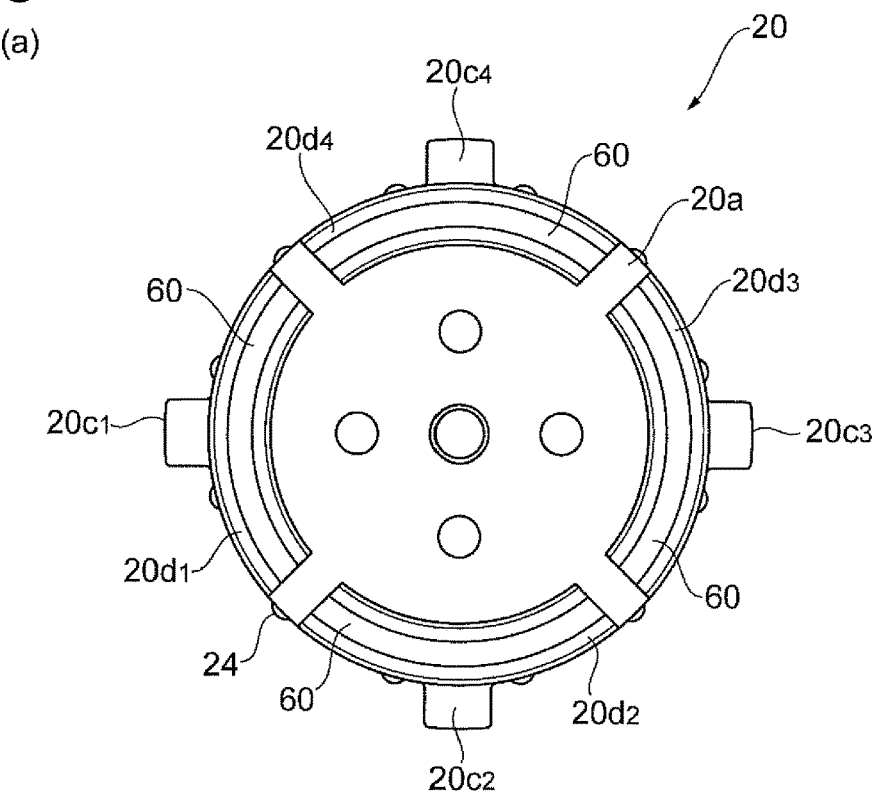
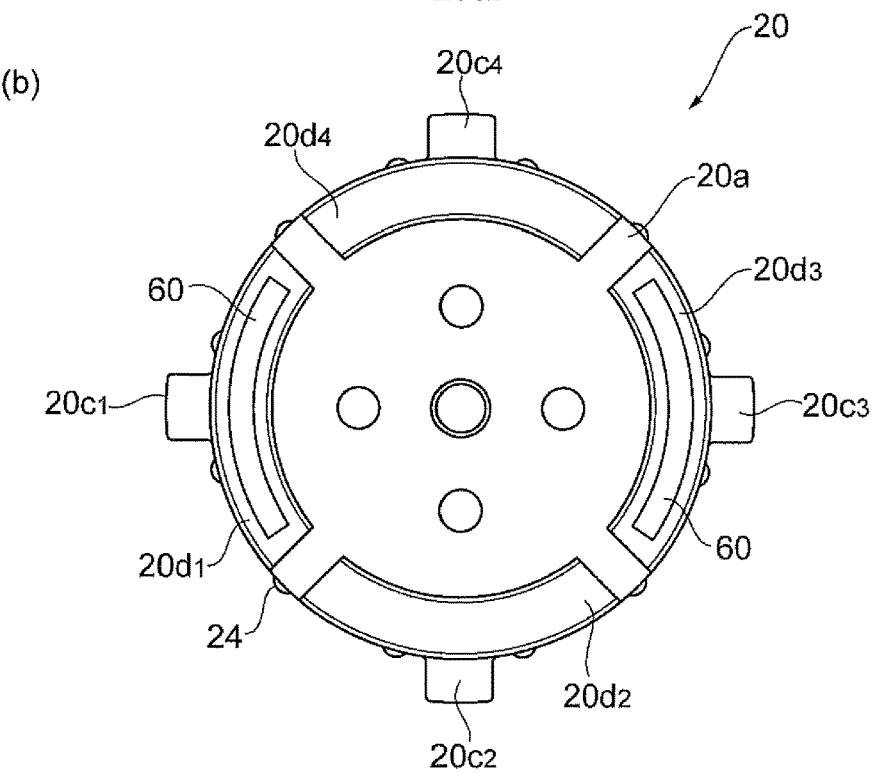

Fig.33
(a)
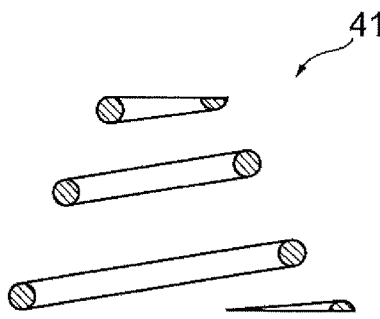
(b)
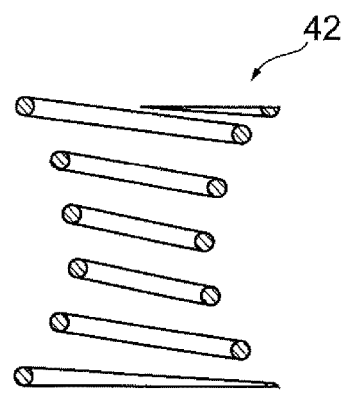
(c)
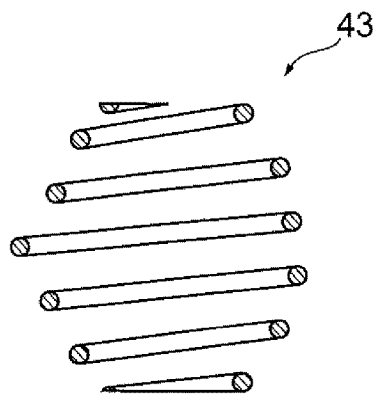
(d)
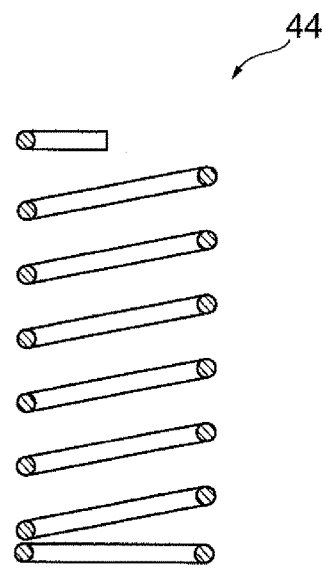

(a)

| | TOTAL WEIGHT[g] | PISTON SPEED [m/s] | TRANSFER RATE OF OVA[%] | | Animal |
|---|---|---|---|---|---|
| | | | AVERAGE(N=3) | STANDARD DEVIATION S.D. | |
| COMPARATIVE EXAMPLE 1 | 1.2 | 8.1 | 37.0 | 17.2 | in vivo rabbit |
| EXAMPLE 1 | 1.2 | 8.1 | 59.9 | 10.8 | in vivo rabbit |
| EXAMPLE 2 | 1.2 | 8.1 | 70.0 | 14.8 | in vivo rabbit |

(b)

APPLICATOR

This is a National Phase Application filed under 35 U.S.C. 371 as a national stage of PCT/JP2014/079272, filed Nov. 4, 2014, an application claiming the benefit of Japanese Application No. 2013-229691, filed Nov. 5, 2013, the content of each of which is hereby incorporated by reference in its entirety.

TECHNICAL FIELD

One aspect of the present invention relates to an applicator for transferring active ingredients into a body through skin by a puncture in the skin.

BACKGROUND ART

Up to now, an applicator that holds a microneedle array by means of a latch mechanism or the like has been known, the microneedle array including a large number of microneedles each having a leading end to which a medical agent or the like is applied (see Patent Literatures 1 to 5). If the microneedle array held by the applicator is caused to collide against skin by disengaging the latch mechanism, the microneedles are stuck into the skin, and active ingredients contained in the medical agent or the like are transferred into the body of an animal (for example, a human) through the skin.

CITATION LIST

Patent Literature

Patent Literature 1: Japanese Patent No. 4659332
Patent Literature 2: Japanese Unexamined Patent Publication No. 2007-516781
Patent Literature 3: International Publication No. WO 2009/107806
Patent Literature 4: International Publication No. WO 00/009184
Patent Literature 5: U.S. Patent Application Publication 2011/276027

SUMMARY OF INVENTION

Technical Problem

Unfortunately, when the microneedle array collides against skin by opening the latch mechanism, elastic force of the skin may cause the microneedle array to bounce off the skin. In that case, the microneedles once stuck into the skin may come off the skin to affect transfer of the active ingredients into a body.

Thus, it is an object of one aspect of the present invention to provide an applicator capable of sufficiently transferring active ingredients into a body.

Solution to Problem

An applicator in accordance with one aspect of the present invention is configured to transfer an active ingredient into a body through skin by a puncture in the skin with microneedles. The applicator comprises a piston plate that is provided on its one main surface with a first protrusion part and at least one second protrusion part. The first protrusion part is provided on its surface with microneedles, and the second protrusion part is provided in a periphery of the first protrusion part while spaced apart from the first protrusion part.

In the applicator in accordance with one aspect of the present invention, the at least one second protrusion part is provided in the periphery of the first protrusion part while spaced apart from the first protrusion part. Thus, even if the first protrusion part collides against skin to cause the skin to undulate (even if undulation is produced in the skin), the undulation is reduced by the second protrusion part. This causes the piston plate not to easily bounce off the skin, and thus the microneedles once stuck into the skin tend to easily stay in the skin. As a result, the active ingredients can be sufficiently transferred into a body.

In the second protrusion part, an adhesive substance with adhesive capability may be provided in at least a part of a surface thereof. In this case, the adhesive substance tends to adhere to the skin when the piston plate collides against the skin. Accordingly, a bounce of the piston plate from the skin can be reduced more.

A plurality of the second protrusion parts may be provided on the piston plate, the plurality of the second protrusion parts being disposed in such a way as to surround the first protrusion part.

The second protrusion part may have an annular shape surrounding the entire periphery of the first protrusion part.

A portion between the first protrusion part and the second protrusion part may form a recessed part recessed from surfaces of the protrusion parts. In this case, undulation of the skin may be absorbed in the recessed part. Accordingly, a bounce of the piston plate from the skin can be reduced further.

An applicator in accordance with another aspect of the present invention is configured to transfer an active ingredient into a body through skin by a puncture in the skin with microneedles. The applicator comprises a piston plate that transmits impact force to a microneedle array in which microneedles are provided in a predetermined region when one main surface of the piston plate collides against the microneedle array. The piston plate includes at least one protrusion part that is provided in the one main surface in such a way as to surround the microneedle array while spaced apart from the predetermined region of the microneedle array.

In the applicator in accordance with another aspect of the present invention, the at least one protrusion part is provided in the one main surface of the piston plate in such a way as to surround the microneedle array while spaced apart from the predetermined region in the microneedle array. Thus, even if the piston plate collides against the microneedle array previously arranged on the skin to cause the skin to undulate (even if undulation is produced in the skin), the undulation is reduced by the protrusion part. This causes the piston plate not to easily bounce off the skin, and thus the microneedles once stuck into the skin tends to easily stay in the skin. As a result, the active ingredients can be sufficiently transferred into a body.

In the at least one protrusion part, an adhesive substance with adhesive capability may be provided in at least a part of a surface thereof. In this case, the adhesive substance tends to adhere to the skin when the piston plate collides against the skin. Accordingly, a bounce of the piston plate from the skin can be reduced more.

A plurality of the second protrusion parts may be provided on the piston plate, the plurality of the protrusion parts being disposed in such a way as to surround the microneedle array.

The protrusion part may have an annular shape surrounding the entire periphery of the microneedle array.

A portion between the predetermined region in the microneedle array and the protrusion part forms a recessed part recessed from the predetermined region and a surface of the protrusion part. In this case, undulation of the skin may be absorbed in the recessed part. Accordingly, a bounce of the piston plate from the skin can be reduced further.

An applicator in accordance with still another aspect of the present invention is configured to transfer an active ingredient into a body through skin by a puncture in the skin with microneedles. The applicator comprises a piston plate that is provided on its one main surface with a microneedle region where microneedles are located and at least one protrusion part, and the protrusion part is provided in a periphery of the microneedle region while spaced apart from the microneedle region.

In the applicator in accordance with still another aspect of the present invention, the at least one protrusion part is provided in the periphery of the microneedle region while spaced apart from the microneedle region. Thus, even if the surface with the microneedles collides against skin to cause the skin to undulate (even if undulation is produced in the skin), the undulation is reduced by the protrusion part. This causes the piston plate not to easily bounce off the skin, and thus the microneedles once stuck into the skin tends to easily stay in the skin. As a result, the active ingredients can be sufficiently transferred into a body. The "microneedle region" in this aspect of the present invention is a concept corresponding to the "first protrusion part" in the application as a basis of priority claim of the present application, as well as the "at least one protrusion part" is a concept corresponding to the "at least one second protrusion part" in the base application.

The first protrusion part is provided in the microneedle region, and at least one protrusion part is provided as the second protrusion part. The microneedles are provided in a surface of the first protrusion part, and the second protrusion part may be provided in the periphery of the first protrusion part while spaced apart from the first protrusion part.

In the second protrusion part, an adhesive substance with adhesive capability may be provided in at least a part of a surface thereof. In this case, the adhesive substance tends to adhere to the skin when the piston plate collides against the skin. Accordingly, a bounce of the piston plate from the skin can be reduced more.

A plurality of the second protrusion parts may be provided on the piston plate, the plurality of the second protrusion parts being disposed in such a way as to surround the first protrusion part.

The second protrusion part may have an annular shape surrounding the entire periphery of the first protrusion part.

A portion between the first protrusion part and the second protrusion part forms a recessed part recessed from surfaces of the protrusion parts. In this case, undulation of the skin may be absorbed in the recessed part. Accordingly, a bounce of the piston plate from the skin can be reduced further.

A difference in height between a leading end surface of the at least one protrusion part and a leading end of the microneedle protruding outward from the leading end surface may be 0 mm or more. Setting the difference in height in this way enables improving puncture performance.

The difference in height may be not less than 0 mm and not more than 1.0 mm. Setting the difference in height in this way enables improving the puncture performance.

A value D/F may be not less than 0.0 and not more than 1.4, where D is the difference in height, and F is an average length of the microneedles. Setting the difference in height in this way enables improving the puncture performance.

The value D/F also may be not less than 1.0 and not more than 1.4. Setting the difference in height in this way enables improving the puncture performance.

Advantageous Effects of Invention

According to one aspect of the present invention, it is possible to provide an applicator capable of sufficiently transferring active ingredients into a body.

BRIEF DESCRIPTION OF DRAWINGS

FIG. 7 is a right-side view of the applicator in accordance with the present embodiment.

FIG. 8 is a left-side view of the applicator in accordance with the present embodiment.

FIG. 27 shows a state where the piston plate collides against skin.

FIG. 28 shows another example of the piston plate.

FIG. 29 shows still another example of the piston plate.

FIG. 33 shows another example of the coil spring.

DESCRIPTION OF EMBODIMENTS

Figure 1:
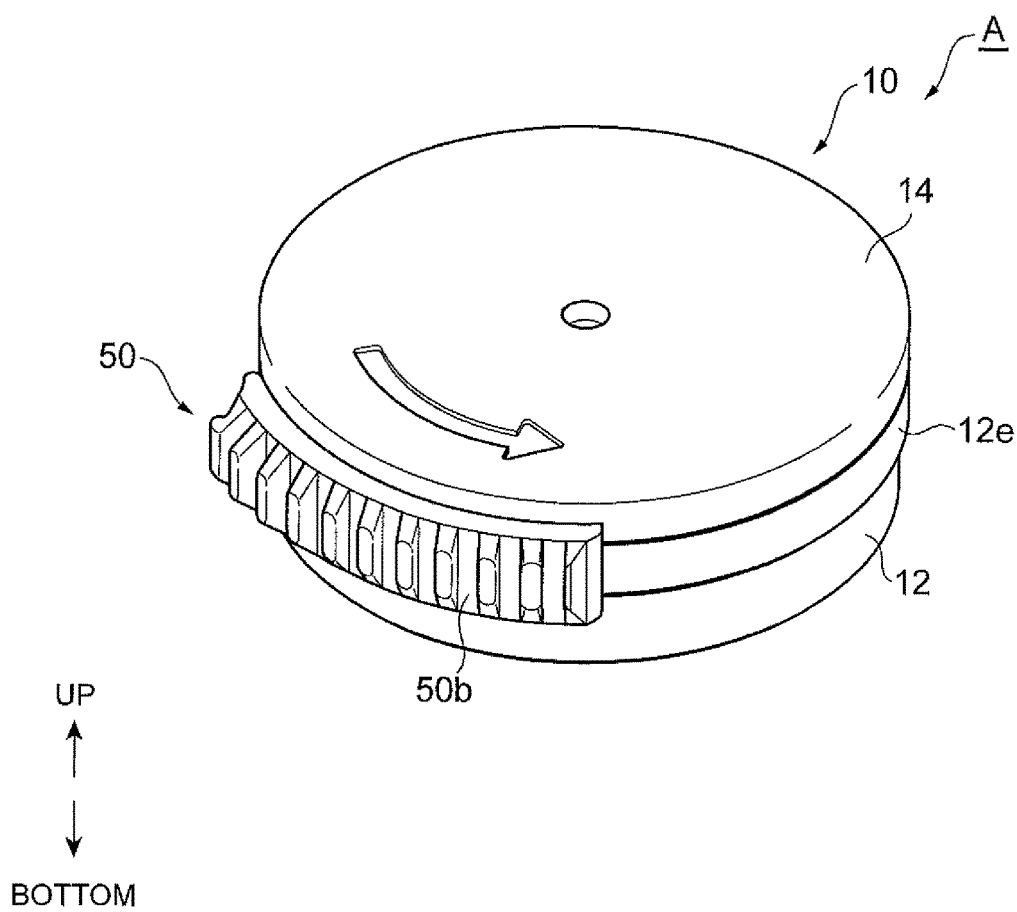
FIG. 1 is a perspective view of an applicator in accordance with the present embodiment when viewed from above.
Figure 2:
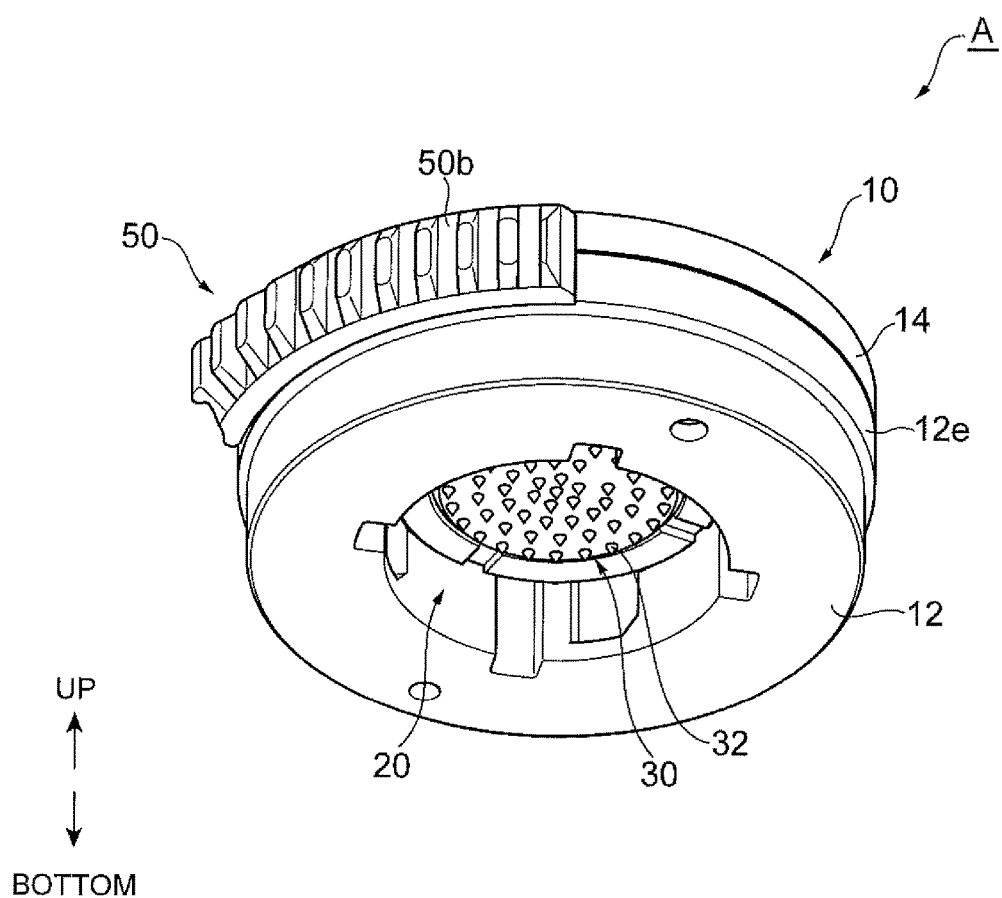
FIG. 2 is a perspective view of the applicator in accordance with the present embodiment when viewed from below.
Figure 3:
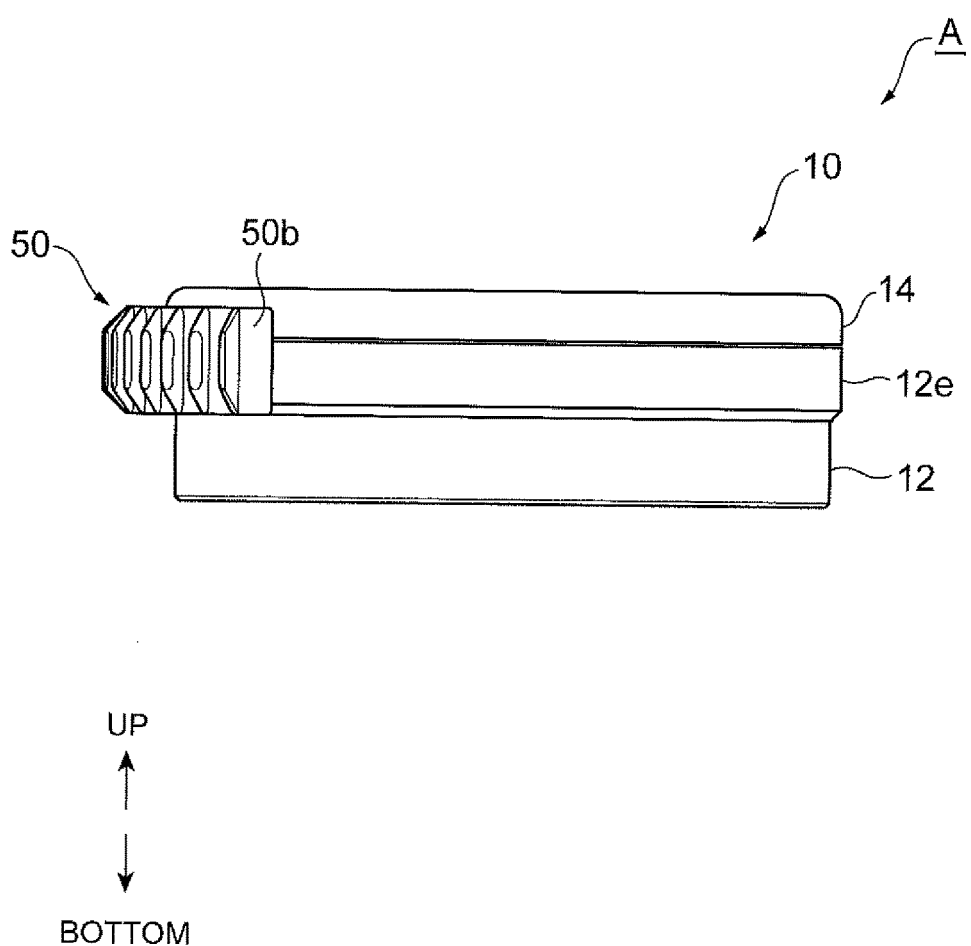
FIG. 3 is a front view of the applicator in accordance with the present embodiment.
Figure 4:
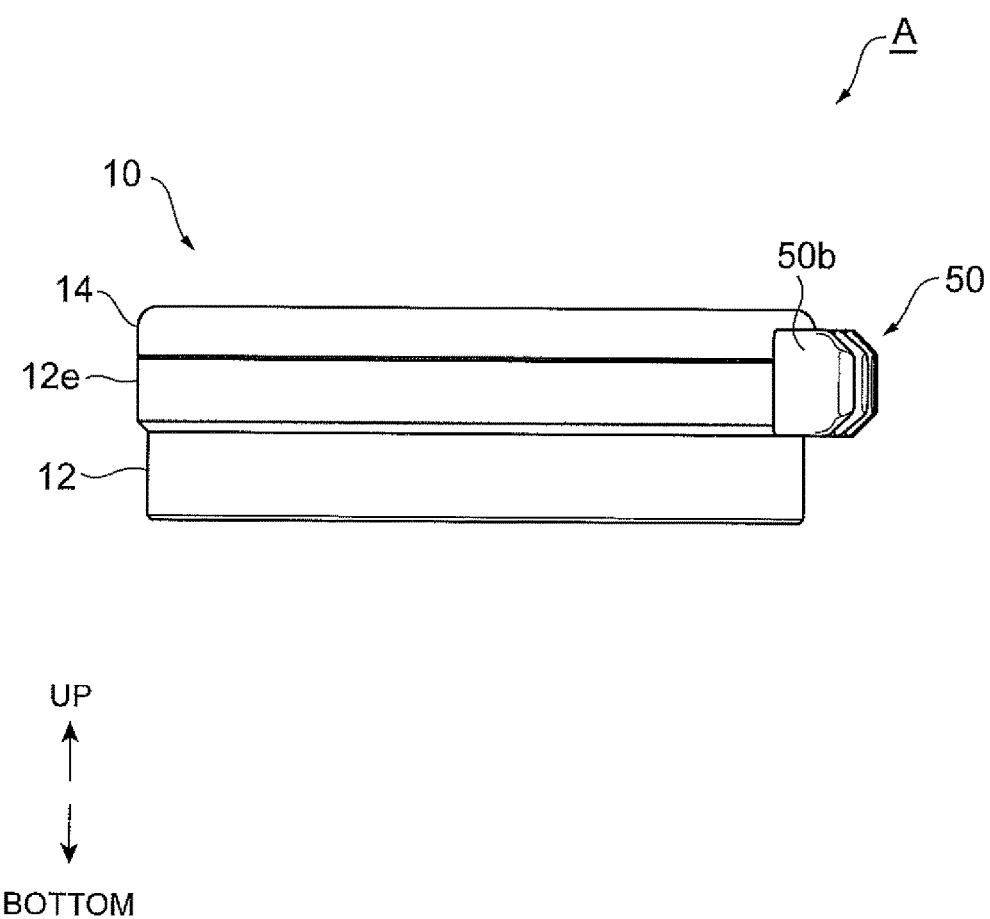
FIG. 4 is a rear view of the applicator in accordance with the present embodiment.
Figure 5:
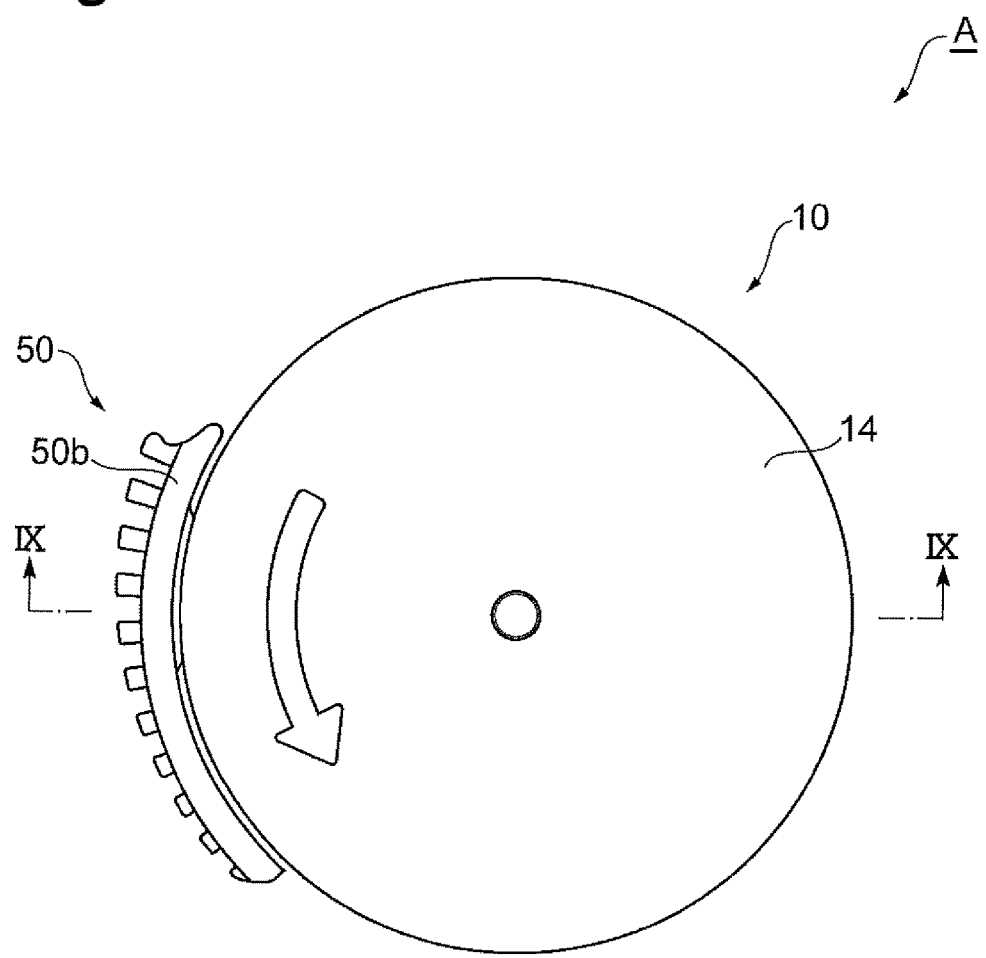
FIG. 5 is a plan view of the applicator in accordance with the present embodiment.
Figure 6:
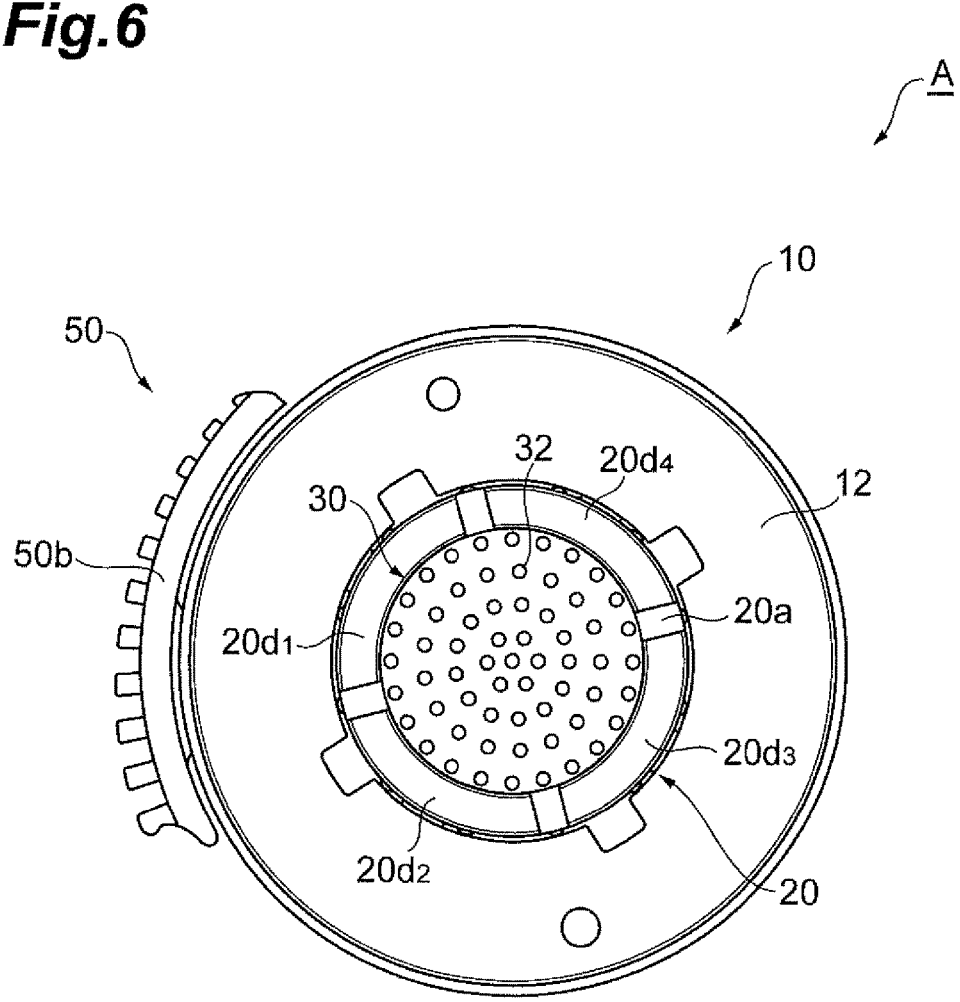
FIG. 6 is a bottom view of the applicator in accordance with the present embodiment.

Embodiments of the present invention are described with reference to the drawings. The following present embodiments are given as examples for describing the present invention, and the present invention is not limited to the following contents. In the following description, the same elements or elements having the same functions are denoted by the same reference signs, and redundant description is omitted.

[1] Configuration of Applicator

A configuration of an applicator A in accordance with a first embodiment is described with reference to FIGS. 1 to 10. In the following description, the term "top" corresponds to the upper direction of FIGS. 1, 2 to 4, 7 to 10, 13, and 17 to 19, and the term "bottom" corresponds to the lower direction of FIGS. 1, 2 to 4, 7 to 10, 13, and 17 to 19. That is, the top-bottom direction corresponds to the height direction of the applicator A.

The applicator A is a device for transferring active ingredients of a medical agent or the like into the body of an animal such as a human through skin of the animal by a puncture in the skin with microneedles 32 (to be described later in detail). The applicator A includes a casing 10, a piston plate 20, a microneedle array 30, a conical coil spring 40, and a release member 50.

As shown in FIGS. 1 to 10, the casing 10 includes a main body part 12 having the central axis that extends along the top-bottom direction and having a cylindrical shape, and a cover part 14 arranged on the upper end side of the main body part 12. The casing 10 has strength high enough to maintain the biasing force of the conical coil spring 40 (to be described later in detail). Examples of the material of the casing 10 include polycarbonate resin, ABS resin, and synthetic or natural resin materials such as polystyrene, polypropylene, and polyacetal (POM), and can also include silicon, silicon dioxide, ceramics, and metal (such as stainless steel, titanium, nickel, molybdenum, chromium, and cobalt). Glass fiber, carbon fiber, and the like may be added to the above-mentioned resin materials for the purpose of increasing the strength and the like.

It is desirable that the applicator A has a shape that enables easy hold and enables easy application (easy puncture) of the microneedles 32 (to be described later) to the skin of the animal (including a human). Thus, the outer shape of the main body part 12 may be other than the cylindrical shape, and may be, for example, multangular or rounded. A recess or a step may be provided on the surface of the main body part 12. A fine groove may be formed on the surface of the main body part 12, or a non-slippery coating layer may be provided thereon, whereby the surface of the main body part 12 may be roughened. A through-hole may be formed in the main body part 12 for the purpose of reducing the air resistance and the weight.

As shown in FIGS. 9 to 12, the main body part 12 includes: an outer wall 12a having a cylindrical shape; interior inner walls $12b_1$ to $12b_4$ each having a circular arc-like shape; exterior inner walls $12c_1$ to $12c_4$ each having a circular arc-like shape; and a bottom wall 12d having a circular ring-like shape. A flange member 12e having a circular ring-like shape is provided at a position closer to the upper end (closer to the cover part 14) on the outer circumferential surface of the outer wall 12a. The flange member 12e protrudes outward from the outer circumferential surface of the outer wall 12a. A cutout part 12f that extends in the circumferential direction is provided between the upper end of the outer wall 12a and the flange member 12e.

The interior inner walls $12b_1$ to $12b_4$ are located on the inner side of the outer wall 12a and on a circumference having the same radius. The interior inner walls $12b_1$ to $12b_4$ are arranged in the stated order in the clockwise direction when viewed from the upper end side (the cover part 14 side) of the main body part 12 at predetermined intervals in the circumferential direction. That is, the interior inner wall $12b_1$ and the interior inner wall $12b_2$ are spaced apart from each other at a predetermined interval in the circumferential direction, the interior inner wall $12b_2$ and the interior inner wall $12b_3$ are spaced apart from each other at a predetermined interval in the circumferential direction, the interior inner wall $12b_3$ and the interior inner wall $12b_4$ are spaced apart from each other at a predetermined interval in the circumferential direction, and the interior inner wall $12b_4$ and the interior inner wall $12b_1$ are spaced apart from each other at a predetermined interval in the circumferential direction.

The circle formed by the interior inner walls $12b_1$ to $12b_4$ can be set to be equivalent to or slightly larger than the outer diameter of a main body 20a (to be described later) of the piston plate 20. A diameter of the circle formed by the interior inner walls $12b_1$ to $12b_4$ on a lower side (bottom wall 12d side) may be less than that on an upper side (cover part 14 side), or may be set to gradually decrease toward the lower side in the top-bottom direction (a center axial direction of the main body part 12). In this case, when the piston plate 20 moves from the upper side toward the lower side, posture of the piston plate 20 can be easily maintained. An interval between the interior inner walls adjacent to each other in the circumferential direction among the interior inner walls $12b_1$ to $12b_4$ can be set to be equivalent to or slightly larger than width of protrusions $20c_1$ to $20c_4$ (to be described later) of the piston plate 20. In the present embodiment, the central axis of the interior inner walls $12b_1$ to $12b_4$ is substantially coincident with the central axis of the outer wall 12a (main body part 12), but does not need to be coincident therewith.

A portion of the upper end of the interior inner wall $12b_1$ is cut out, the portion being closer to the interior inner wall $12b_4$. More specifically, the interior inner wall $12b_1$ includes: a first portion $12b_{11}$ having the upper end whose position is equivalent to the position of the upper end of the outer wall 12a; and a second portion $12b_{12}$ having the upper end whose position is closer to the bottom wall 12d than the first portion $12b_{11}$, in the top-bottom direction (the central axis direction of the main body part 12). That is, the first portion $12b_{11}$ and the second portion $12b_{12}$ form a step in the circumferential direction. The interior inner wall $12b_1$ and the outer wall $12a$ are coupled to each other by a coupling wall $12g_1$, whereby the rigidities of the two walls are enhanced. The position of the upper end of the coupling wall $12g_1$ is equivalent to the position of the upper end of the first portion $12b_{11}$. The interior inner wall $12b_1$, the outer wall $12a$, and the coupling wall $12g_1$ can be integrally shaped.

A portion of the upper end of the interior inner wall $12b_2$ is cut out, the portion being closer to the interior inner wall $12b_1$. A portion of the upper end of the interior inner wall $12b_3$ is cut out, the portion being closer to the interior inner wall $12b_2$. A portion of the upper end of the interior inner wall $12b_4$ is cut out, the portion being closer to the interior inner wall $12b_3$. Structure of the interior inner walls $12b_2$ to $12b_4$ is the same as that of the interior inner wall $12b_1$. Specifically, the interior inner wall $12b_2$ includes first and second portions $12b_{21}$ and $12b_{22}$. The interior inner wall $12b_3$ includes first and second portions $12b_{31}$ and $12b_{32}$. The interior inner wall $12b_4$ includes first and second portions $12b_{41}$ and $12b_{42}$. As with the coupling wall $12g_1$, coupling walls $12g_2$ to $12g_4$ couple the interior inner walls $12b_2$ to $12b_4$ to the outer wall $12a$, respectively.

The exterior inner walls $12c_1$ to $12c_4$ are located between the outer wall $12a$ and the interior inner walls $12b_1$ to $12b_4$ and on a circumference having the same radius. The difference between the radius of the circle formed by the exterior inner walls $12c_1$ to $12c_4$ and the radius of the circle formed by the interior inner walls $12b_1$ to $12b_4$, that is, the depths of groove parts G1 to G4 (to be described later) can be set to be equivalent to or slightly larger than the protruding lengths of the protrusions $20c_1$ to $20c_4$ (to be described later) of the piston plate 20. The exterior inner walls $12c_1$ to $12c_4$ are arranged in the stated order in the clockwise direction when viewed from the upper end side (the cover part 14 side) thereof at predetermined intervals in the circumferential direction. That is, the exterior inner wall $12c_1$ and the exterior inner wall $12c_2$ are spaced apart from each other at a predetermined interval in the circumferential direction, the exterior inner wall $12c_2$ and the exterior inner wall $12c_3$ are spaced apart from each other at a predetermined interval in the circumferential direction, the exterior inner wall $12c_3$ and the exterior inner wall $12c_4$ are spaced apart from each other at a predetermined interval in the circumferential direction, and the exterior inner wall $12c_4$ and the exterior inner wall $12c_1$ are spaced apart from each other at a predetermined interval in the circumferential direction.

A lateral part of the exterior inner wall $12c_1$ is connected to lateral parts of the interior inner walls $12b_1$ and $12b_2$. The exterior inner wall $12c_1$ and the interior inner walls $12b_1$ and $12b_2$ can be integrally shaped. Thus, the exterior inner wall $12c_1$ and the interior inner walls $12b_1$ and $12b_2$ form the groove part G1 that extends in the top-bottom direction, on the inner circumferential surface of the main body part 12. That is, the groove part G1 is adjacent to the second portion $12b_{22}$ of the interior inner wall $12b_2$. The position of the upper end of the exterior inner wall $12c_1$ is equivalent to the position of the upper end of the outer wall $12a$, in the top-bottom direction. The exterior inner wall $12c_1$ and the outer wall $12a$ are coupled to each other by a coupling wall $12g_5$, whereby the rigidities of the two walls are enhanced. The position of the upper end of the coupling wall $12g_5$ is equivalent to the position of the upper end of the exterior inner wall $12c_1$. The exterior inner wall $12c_1$, the outer wall $12a$, and the coupling wall $12g_5$ can be integrally shaped.

The exterior inner walls $12c_2$ to $12c_4$ each also have the almost same structure as that of the exterior inner wall $12c_1$. Thus, the exterior inner wall $12c_2$ and the interior inner walls $12b_2$ and $12b_3$ form the groove part G2 that extends in the top-bottom direction, on the inner circumferential surface of the main body part 12. The exterior inner wall $12c_3$ and the interior inner walls $12b_3$ and $12b_4$ form the groove part G3 that extends in the top-bottom direction, on the inner circumferential surface of the main body part 12. The exterior inner wall $12c_3$ and the interior inner walls $12b_3$ and $12b_4$ form the groove part G3 that extends in the top-bottom direction, on the inner circumferential surface of the main body part 12. That is, the groove part G2 is adjacent to the second portion $12b_{32}$ of the interior inner wall $12b_3$. The groove part G3 is adjacent to the second portion $12b_{42}$ of the interior inner wall $12b_4$. The groove part G4 is adjacent to the second portion $12b_{12}$ of the interior inner wall $12b_1$.

A position of an upper end of each of the exterior inner walls $12c_3$ and $12c_4$ is different from that of the exterior inner wall $12c_1$. Specifically, the position of the upper end of the exterior inner wall $12c_3$ is equivalent to the position of the upper end of the adjacent second portion $12b_{42}$ of the interior inner wall $12b_4$, in the top-bottom direction. That is, the upper end of the exterior inner wall $12c_3$ is located closer to the bottom wall $12d$ than the upper end of the outer wall $12a$. The position of the upper end of the exterior inner wall $12c_4$ is also equivalent to the position of the upper end of the exterior inner wall $12c_3$.

As with the coupling wall $12g_5$, the coupling walls $12g_6$ to $12g_8$ couple the exterior inner walls $12c_2$ to $12b_4$ to the outer wall $12a$, respectively. A position of an upper end of the coupling wall $12g_7$ is different from that of the coupling wall $12g_5$. Specifically, the position of the upper end of the coupling wall $12g_7$ is located closer to the bottom wall $12d$ than the position of the upper end of the exterior inner wall $12c_3$. Accordingly, in a cross section of the exterior inner wall $12c_3$, the coupling wall $12g_7$, and the outer wall $12a$, a portion of the coupling wall $12g_7$ is observed as a recessed part.

The bottom wall $12d$ is connected to a lower end of the outer wall $12a$, lower ends of the interior inner walls $12b_1$ to $12b_4$, lower ends of the exterior inner walls $12c_1$ to $12c_4$, and lower ends of the coupling walls $12g_1$ to $12g_8$. The outer diameter of the bottom wall $12d$ is equivalent to the diameter of the outer circumference of the outer wall $12a$. The inner diameter of the bottom wall $12d$ is equivalent to the diameter of the circle formed by the inner circumferential surfaces of the interior inner walls $12b_1$ to $12b_4$. Thus, the lower ends of the groove parts G1 to G4 are closed by the bottom wall $12d$ (see FIGS. 9 and 12).

As shown in FIGS. 1 to 10, the cover part 14 includes a top plate $14a$ having a circular shape, and a cylindrical member $14b$ that extends downward from the periphery of the top plate $14a$. The height of the cylindrical member $14b$ can be set to be equivalent to the length from the flange member $12e$ to the upper end on the outer wall $12a$. The cylindrical member $14b$ is provided with a cutout part $14c$ that extends in the circumferential direction. The length of the cutout part $14c$ can be set to the same length as that of the cutout part $12f$ of the outer wall $12a$.

In the completed state of the applicator A, the cover part 14 is attached to the main body part 12. The cover part 14 is attached to the main body part 12 in the state where the cover part 14 is positioned with respect to the main body part 12 such that the cutout part $14c$ of the cover part 14 and the cutout part $12f$ of the outer wall $12a$ are coincident with each other. Thus, the cutout parts $12f$ and $14c$ form a through-hole H (see FIG. 10) that communicates the inside and the outside of the casing 10 with each other. Examples of the adoptable method of attaching the cover part 14 to the main body part 12 include: a method of adhering the cylindrical member 14b of the cover part 14 to the flange member 12e of the main body part 12 with the use of an adhesive, an adhesive sheet, and the like; a method of mechanically engaging the two parts (for example, providing an engagement claw in the cylindrical member 14b, providing an engagement hole in the flange member 12e, and fitting the engagement claw and the engagement hole to each other); a method of pressure-bonding the cover part 14 to the main body part 12 (for example, setting the diameter of the cylindrical member 14b of the cover part 14 to be smaller than the outer diameter of the main body part 12 and press-fitting the cover part 14 to the main body part 12); and a method of welding the cover part 14 to the main body part 12 (for example, heating and melting the cylindrical member 14b and the flange member 12e and then cooling and integrating the two members).

The piston plate 20 is housed in the main body part 12, and is movable in the top-bottom direction along the central axis of the main body part 12 inside of the main body part 12. The material of the piston plate 20 may be the same as the material of the casing 10, and may be the same as the material (to be described later) of the microneedle array 30. As shown in FIGS. 9 to 11, and 13 to 19, the piston plate 20 includes the disc-like main body 20a, and a cylindrical member 20b that extends upward from the periphery of the main body 20a. An opening, a groove, a through-hole, or the like may be formed in the main body 20a for the purpose of reducing the air resistance and the weight of the piston plate 20. Alternatively, an elongated protrusion or the like may be provided on the upper surface (the surface on which the conical coil spring 40 is arranged) of the main body 20a for the purpose of improving the rigidity of the piston plate 20.

The inner diameter of the cylindrical member 20b is set to be larger than a maximum diameter D1 (to be described later) of the conical coil spring 40. The height of the cylindrical member 20b is not particularly limited as long as the cylindrical member 20b can function as such a stopper that prevents the conical coil spring 40 from dropping off the piston plate 20 during its movement in the radial direction. For example, in the case where the height of the applicator A is desired to be minimized, the height of the cylindrical member 20b can be set to be equivalent to the thickness of a metal wire that forms the conical coil spring 40. In the case where the stopper for the conical coil spring 40 is not necessary, the piston plate 20 does not need to include the cylindrical member 20b. Even in the case where the piston plate 20 does not include the cylindrical member 20b, if a ring-like groove in which the metal wire that forms the conical coil spring 40 can be fit is formed in the main body 20a, the function as the stopper for the conical coil spring 40 can be fulfilled by the ring-like groove. In the case where such a stopper for the conical coil spring 40 is provided, a failure in positioning of the conical coil spring 40 with respect to the piston plate 20 can be prevented at the time of arranging the conical coil spring 40 on the upper surface of the piston plate 20 and then attaching the cover part 14 to the main body part 12 to thereby make the applicator A.

The plurality of protrusions (in the present embodiment, four protrusions) $20c_1$ to $20c_4$ are provided in the periphery (on the outer circumferential surface) of the piston plate 20, and the protrusions $20c_1$ to $20c_4$ each protrude outward in the radial direction (the direction that intersects with the thickness direction of the piston plate). The protrusions $20c_1$ to $20c_4$ are arranged in the stated order in the clockwise direction when viewed from above (the upper surface side of the piston plate 20 on which the conical coil spring 40 is placed) at predetermined intervals in the circumferential direction. In the present embodiment, the protrusions $20c_1$ to $20c_4$ each have a quadrangular prism shape. Alternatively, the protrusions $20c_1$ to $20c_4$ may have other shapes (for example, a columnar shape, a polygonal prism shape, a deformed pillar shape, a circular cone shape, a polygonal pyramid shape, a truncated circular cone shape, and a truncated polygonal pyramid shape) as long as locking with the second portions $12b_{12}$ to $12b_{42}$ of the interior inner walls $12b_1$ to $12b_4$ is possible and movement in the groove parts G1 to G4 is possible.

The protrusions $20c_1$ to $20c_4$ are movable inside the groove parts G1 to G4, respectively, along extending direction of the groove parts. Thus, the piston plate 20 can be guided in the top-bottom direction along the extending directions of the groove parts G1 to G4 (the axial direction of the main body part 12). In the state where the protrusions $20c_1$ to $20c_4$ are located on the upper end sides of the groove parts G1 to G4, respectively, the protrusions $20c_1$ to $20c_4$ are movable above the second portions $12b_{22}$, $12b_{32}$, $12b_{42}$, and $12b_{12}$, respectively, in the horizontal direction. Thus, the protrusions $20c_1$ to $20c_4$ can be placed on the upper ends of the second portion $12b_{22}$, $12b_{32}$, $12b_{42}$, and $12b_{12}$, adjacent to the groove parts G1 to G4, respectively.

The upper ends of the second portions $12b_{12}$ to $12b_{42}$ of the interior inner walls $12b_1$ to $12b_4$ may extend in the circumferential direction so as to be parallel to a horizontal plane, and may be inclined to the horizontal plane, in the circumferential direction. In particular, the upper ends of the second portions $12b_{12}$ to $12b_{42}$ may be inclined such that the heights thereof become larger toward the respective adjacent groove parts G1 to G4. In this case, when the protrusions $20c_1$ to $20c_4$ placed on the upper ends of the second portions $12b_{12}$ to $12b_{42}$ move toward the groove parts G1 to G4, the protrusions $20c_1$ to $20c_4$ need to climb the slopes of the upper ends of the second portions $12b_{12}$ to $12b_{42}$, respectively. Thus, even if an impact or the like is applied from the outside to the applicator A, the protrusions $20c_1$ to $20c_4$ can be prevented from unintentionally moving into the groove parts G1 to G4.

Figure 13:
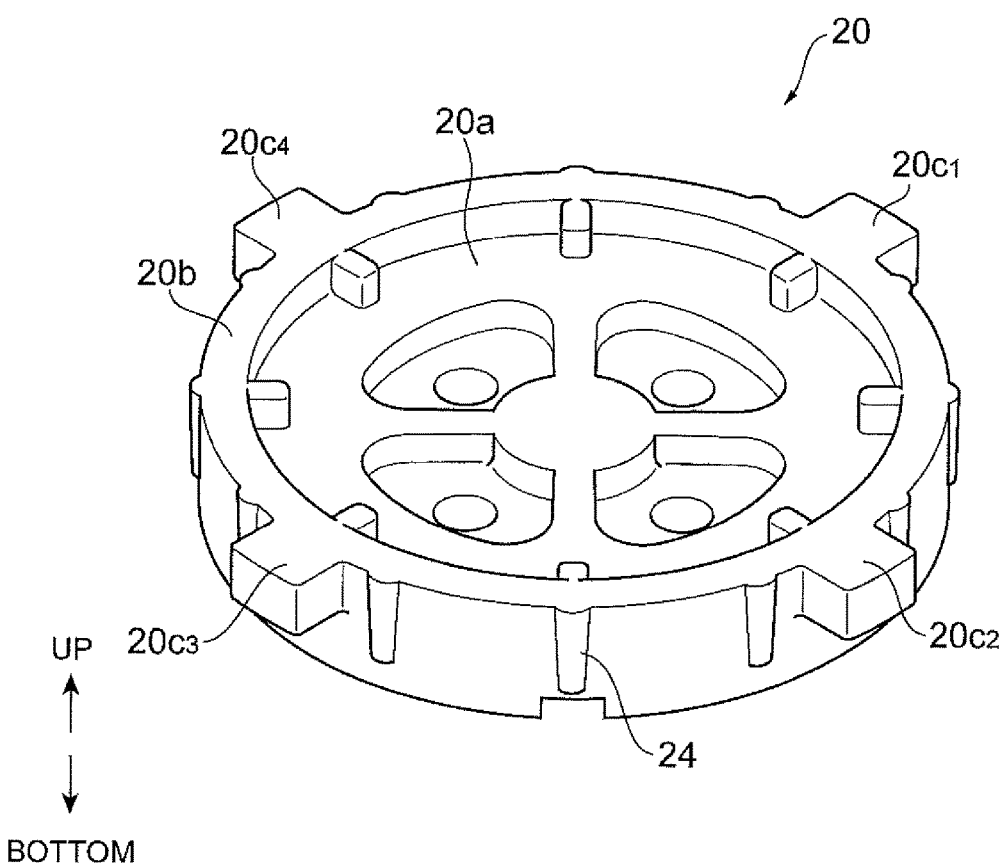
FIG. 13 is a perspective view of a piston plate when viewed from above.
Figure 14:
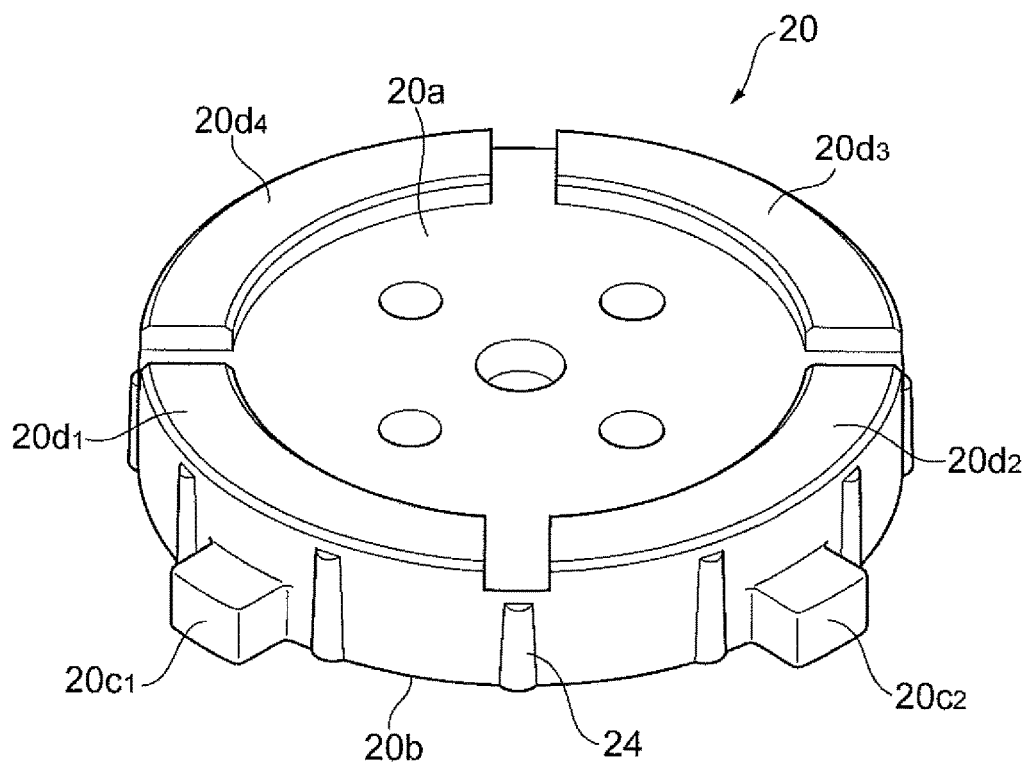
FIG. 14 is a perspective view of the piston plate when viewed from below.
Figure 15:
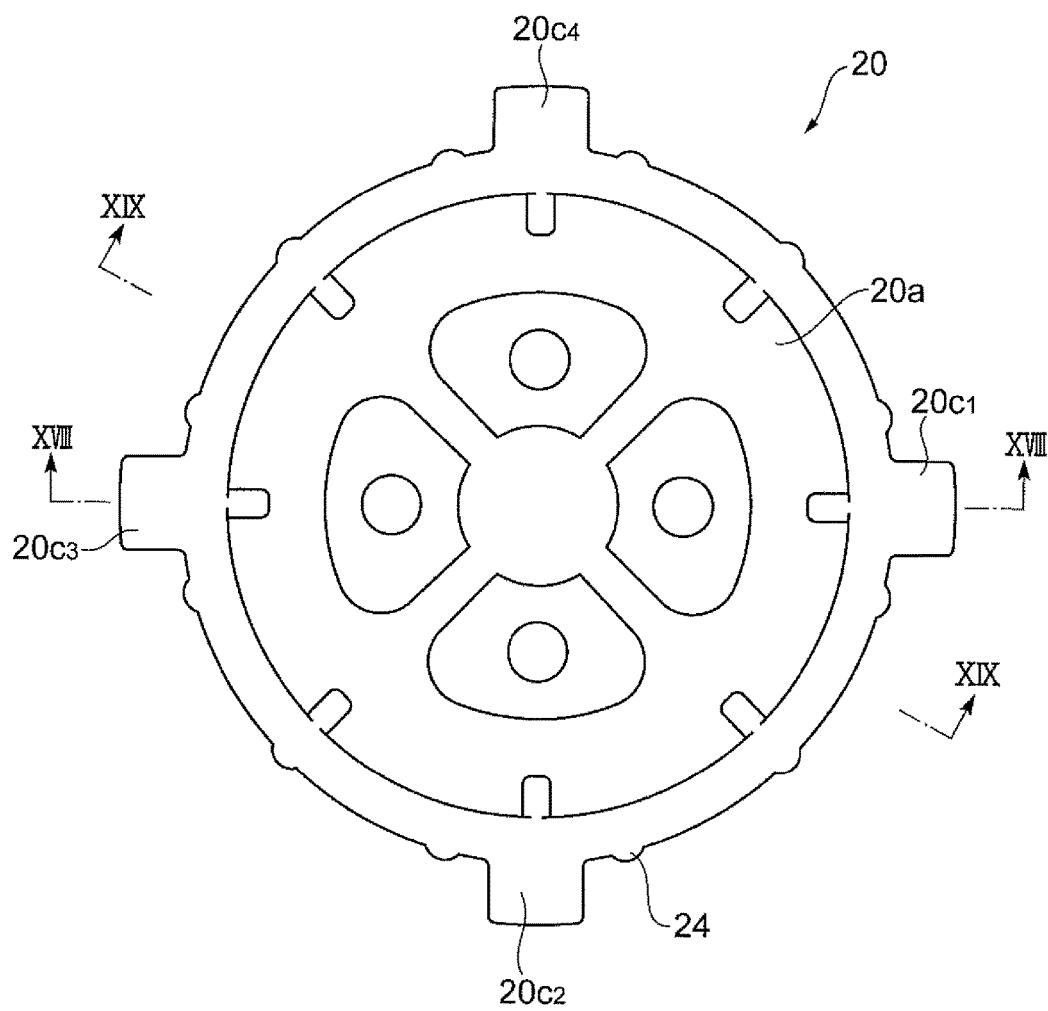
FIG. 15 is a plan view of the piston plate.
Figure 16:
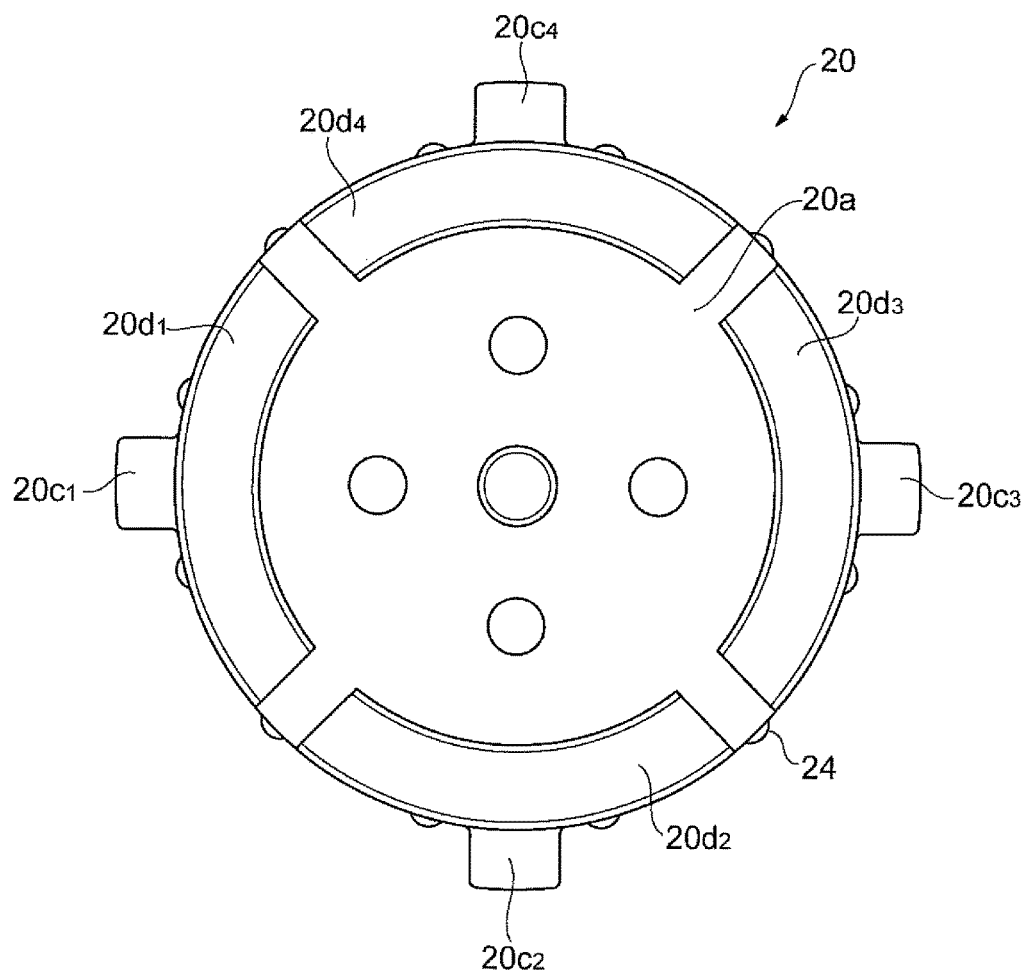
FIG. 16 is a bottom view of the piston plate.
Figure 17:
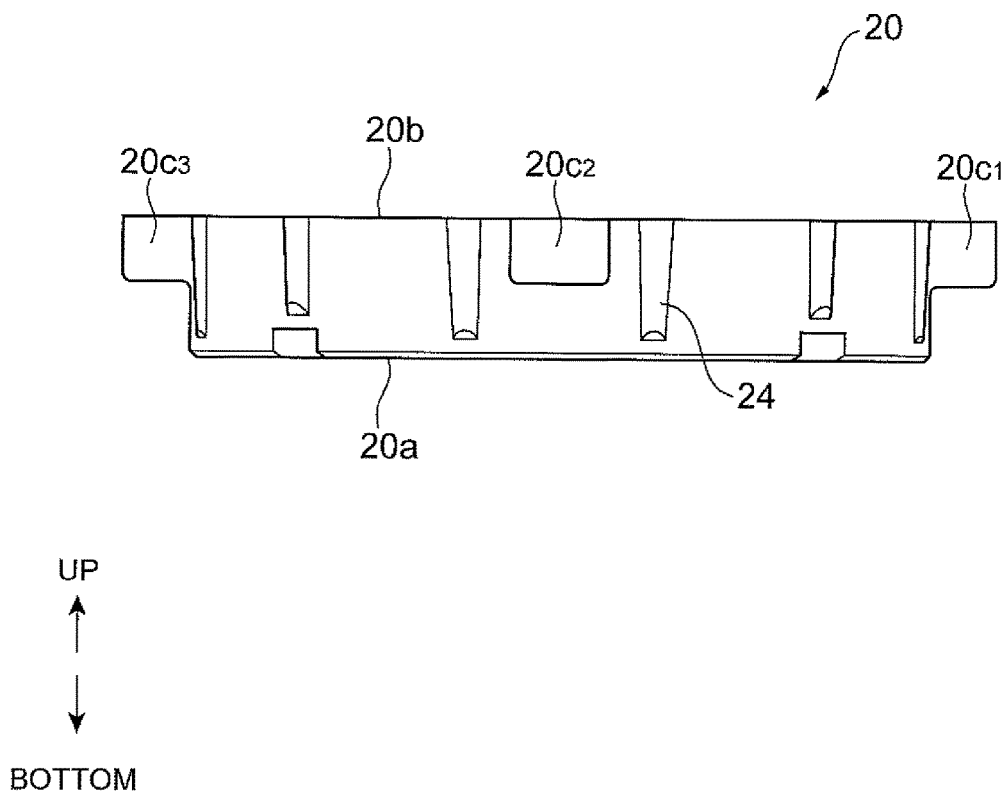
FIG. 17 is a front view of the piston plate.
Figure 18:
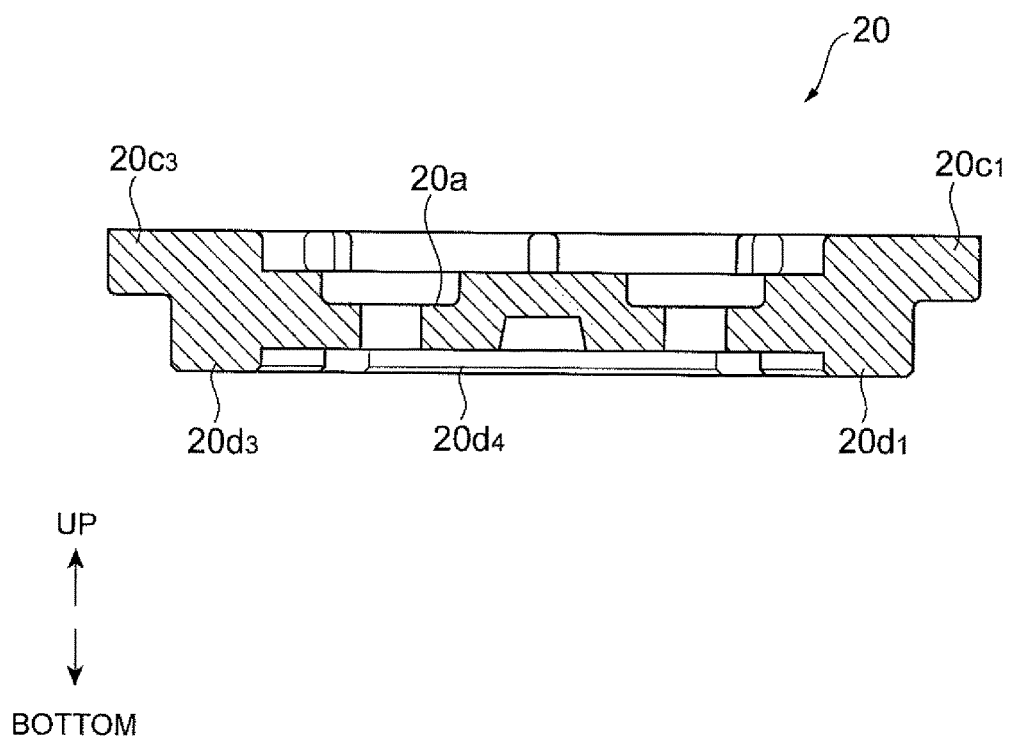
FIG. 18 is a sectional view taken along line XVIII-XVIII in FIG. 15.
Figure 19:
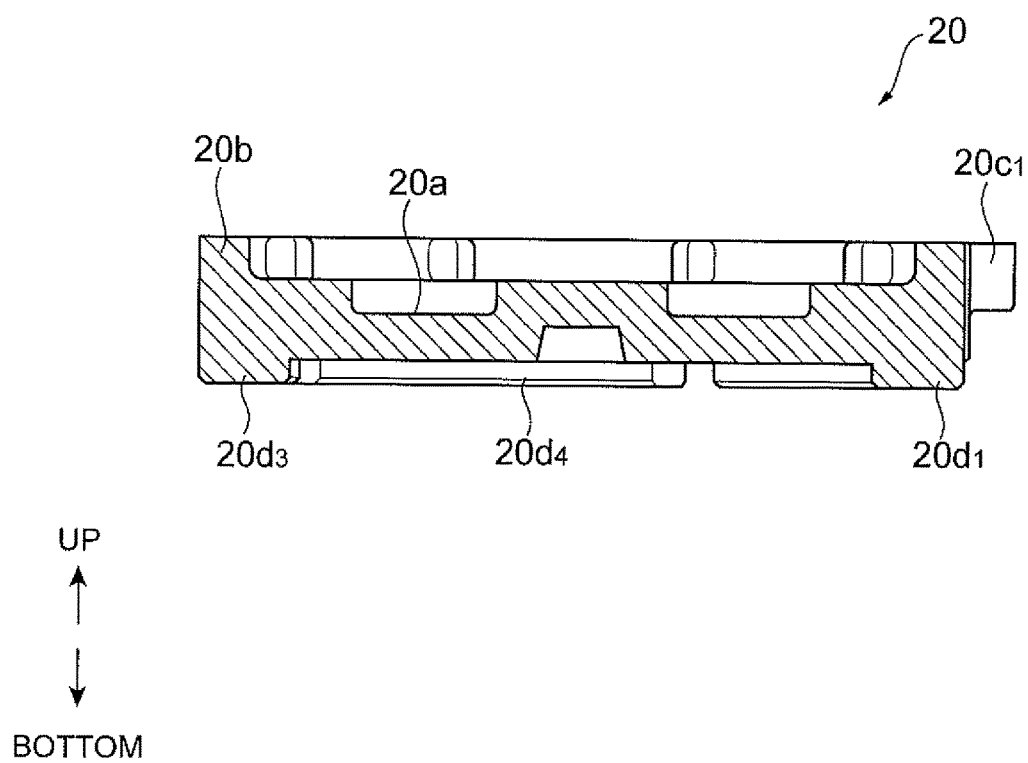
FIG. 19 is a sectional view taken along line XIX-XIX in FIG. 15.

As shown in FIGS. 13, 14, and the like, a plurality of ribs 24 extending in the top-bottom direction is provided in the periphery (outer circumferential surface) of the piston plate 20. The rib 24 is formed in the shape of a semicircular column, or a shape corresponding to one of two pieces formed by dividing a column into the two pieces in a plane along its central axis. In the present embodiment, a diameter of the rib 24 decreases downward. The plurality of ribs 24 are arranged around the piston plate 20 at predetermined intervals, and thus when the piston plate 20 moves from an upper side toward a lower side, posture of the piston plate 20 is maintained almost horizontally, as well as the piston plate 20 slides (falls) almost straightly in the main body part 12 along the central axis of the main body part 12. Accordingly, the piston plate 20 can be guided more reliably.

A plurality of protrusion parts (the second protrusion parts that are four protrusion parts in the present embodiment) $20d_1$ to $20d_4$ extending downward from the periphery of the main body 20a is provided on the lower surface (the surface opposite to the upper surface) of the main body 20a. The protrusion parts $20d_1$ to $20d_4$ each have a circular arc-like shape when viewed from below, and are located on a circumference having the same radius. The protrusion parts $20d_1$ to $20d_4$ are arranged in the stated order in the counterclockwise direction when viewed from below at predetermined intervals in the circumferential direction. That is, the protrusion part $20d_1$ and the protrusion part $20d_2$ are spaced apart from each other at a predetermined interval in the circumferential direction, the protrusion part $20d_2$ and the protrusion part $20d_3$ are spaced apart from each other at a predetermined interval in the circumferential direction, the protrusion part $20d_3$ and the protrusion part $20d_4$ are spaced apart from each other at a predetermined interval in the circumferential direction, and the protrusion part $20d_4$ and the protrusion part $20d_1$ are spaced apart from each other at a predetermined interval in the circumferential direction.

As shown in FIGS. 9, 10, 20, and 21, the microneedle array 30 includes a disc-like substrate 31, a disk-like protrusion part (first protrusion part) 33 provided on one main surface (lower surface) of the substrate 31, and a plurality of microneedles 32 provided in a protruding manner on a surface of the protrusion part 33. The substrate 31 is a foundation for supporting the protrusion part 33. An outer diameter of the substrate 31 can be set to be equivalent to or slightly smaller than an inner diameter of a circle formed by the protrusion parts $20d_1$ to $20d_4$. Thus, the microneedle array 30 can be arranged inside the protrusion parts $20d_1$ to $20d_4$. The outer diameter of the substrate 31 can be set to be larger than an outer diameter of the protrusion part 33. A central axis of the substrate 31 is substantially coincident with a central axis of the protrusion part 33, but does not necessarily need to be coincident therewith. Accordingly, the substrate 31 protrudes outward from the protrusion part 33 in a radial direction of the substrate 31.

Figure 9:
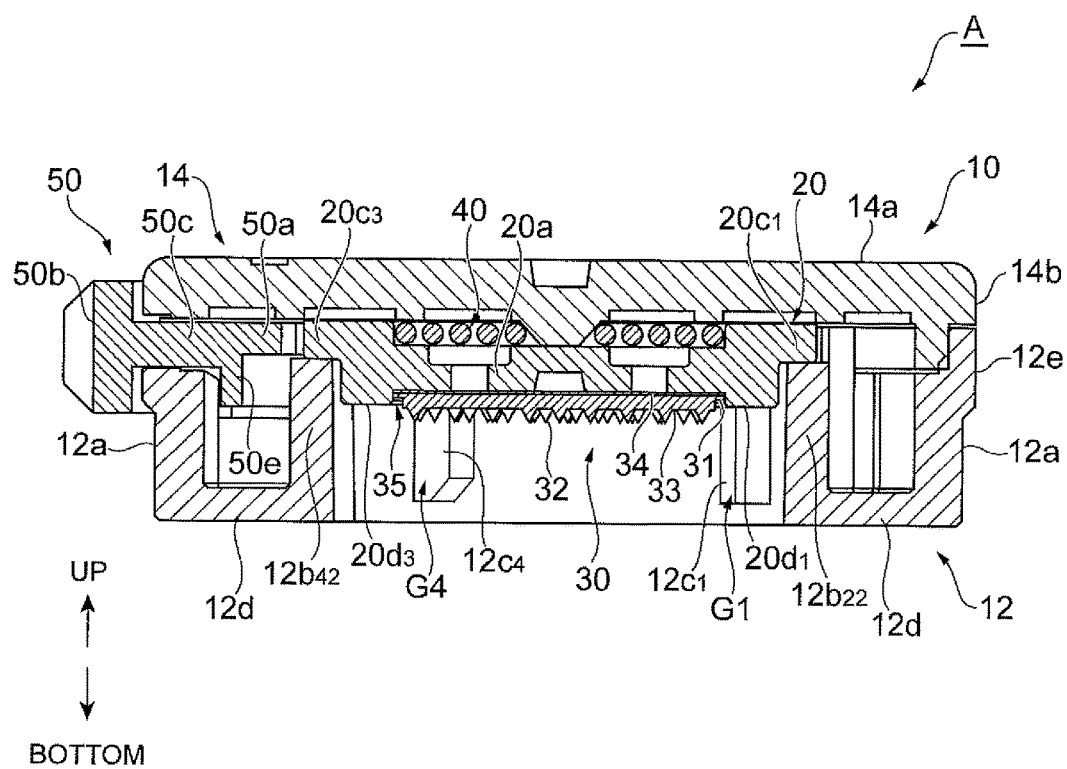
FIG. 9 is a sectional view taken along line IX-IX in FIG. 5.

The substrate 31 has the other main surface (upper surface) attached to the lower surface of the main body 20a of the piston plate 20 (see FIG. 9). That is, the microneedle array 30 is integrated with the piston plate 20. Examples of the adoptable method of attaching the substrate 31 to the piston plate 20 include: a method of mechanically integrating the substrate 31 with the piston plate 20; and a method of adhering the substrate 31 to the piston plate 20 with the use of an adhesive, an adhesive sheet, and the like. In the present embodiment, the microneedle array 30 and the piston plate 20 adhere to each other with an adhesive sheet 34. In a state where the microneedle array 30 is attached to the piston plate 20, the surface of the protrusion part 33 (surface for mounting microneedles) is located outward (downward) surfaces of the protrusion parts $20d_1$ to $20d_4$. The substrate 31 protrudes outward (downward) from the protrusion part 33 in the radial direction, and thus the protrusion part 33 and the protrusion parts $20d_1$ to $20d_4$ are spaced apart from each other in the state where the microneedle array 30 is attached to the piston plate 20. A portion between the protrusion part 33 and the protrusion parts $20d_1$ to $20d_4$ forms a recessed part 35 recessed from surfaces of the protrusion parts $20d_1$ to $20d_4$ and the protrusion part 33.

A portion in a lower surface (main surface) of the main body 20a of the piston plate 20, where the microneedle array 30 is attached, is a microneedle region where the microneedles 32 are located. The "microneedle region (where the microneedles are located)" in the present specification is a part of the piston plate, as well as is a region in the piston plate where the microneedles are directly or indirectly arranged. In the present embodiment, the microneedles 32 are not directly provided in the lower surface of the main body 20a, but the microneedle array 30 including the microneedles 32 is attached to the lower surface of the main body 20a of the piston plate 20. Thus, the microneedle region in the present embodiment is a region where the microneedles 32 are indirectly arranged in the piston plate 20.

Figure 20:
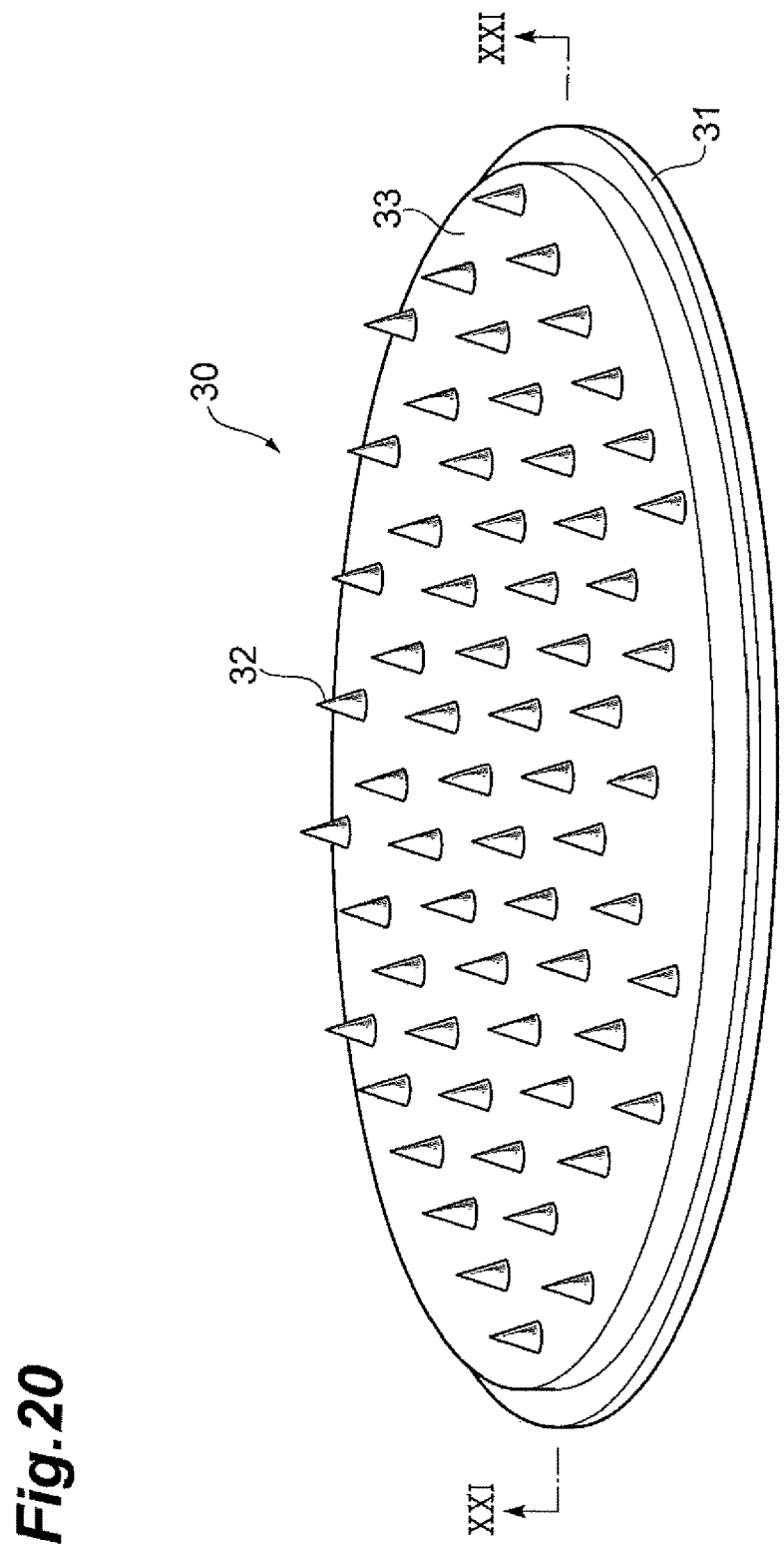
FIG. 20 is a perspective view partially showing a microneedle array.

As shown in FIG. 20, the microneedles 32 are arranged at substantially regular intervals in a zigzag (alternate) pattern on the surface of the substrate 31. Each microneedle 32 is a tapered structure that becomes thinner toward its leading end part from its base end part connected to the protrusion part 33.

Figure 21:
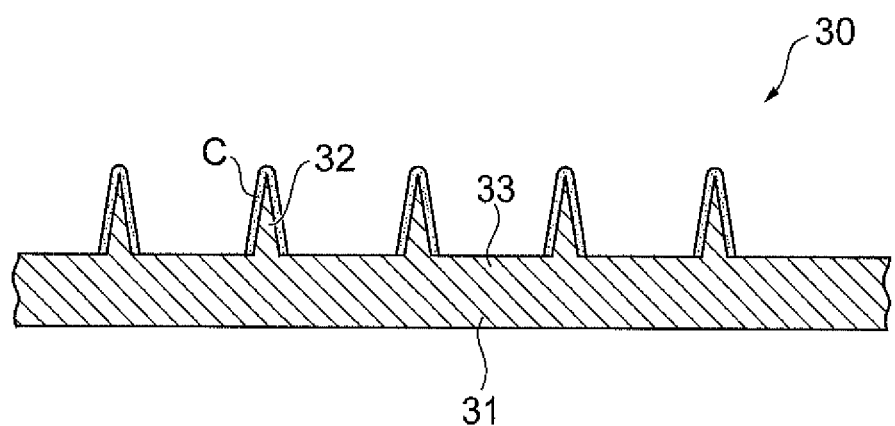
FIG. 21 is a sectional view taken along line XXI-XXI in FIG. 20.

As shown in FIG. 21, coating C with active ingredients may be applied to the substrate 31, the protrusion part 33, and/or the microneedles 32. In the present embodiment, the coating C is obtained by firmly fixing a coating agent (coating liquid) containing active ingredients and purified water and/or coating carriers to the entirety or a part of the surface of each of the substrate 31, the protrusion part 33, and/or the microneedles 32. That is, the coating C is integrated with the microneedles 32. Although extent of integration can be appropriately set, for example, the coating C can flow in a surface of each of the microneedles 32, or the coating C can be solidified to the extent that the coating C itself serves as a needle. The "firmly fixing" here refers to maintaining the state where the coating liquid substantially uniformly adheres to a target. Immediately after the coating, the coating liquid is firmly fixed in a dried state according to a known drying method such as air drying, vacuum drying, freeze drying, and combinations thereof.

The active ingredients used in the present embodiment are not particularly limited, and are selected from the group consisting of antioxidants, free radical scavengers, moisturizers, depigmentation agents, fat regulating agents, UV reflective agents, humectants, antibacterial agents, antiallergic drugs, anti-acne agents, anti-aging agents, anti-wrinkling agents, bactericides, analgesics, antitussives, antipruritics, local anesthetics, anti-hair loss agents, hair growth promoting agents, hair growth inhibitor agents, dandruff inhibitors, antihistamines, keratolytic agents, anti-inflammatory agents, anti-infectives, antiemetics, anticholinergics, vasoconstrictors, vasodilators, wound healing promoters, peptides, polypeptides, proteins, deodorants, antiperspirants, skin emollients, tanning agents, skin lightening agents, antifungals, hemorrhoidal preparations, make-up preparations, vitamins, amino acids, amino acid derivatives, cell turnover enhancers, immunostimulants, DNAs, RNAs, vaccines, low molecular peptides, sugar, nucleic acids, hypnotics/sedatives, antipyretic antiphlogistic analgetic agents, steroidal antiphlogistics, stimulants/psychostimulants, psychoneurotic drugs, hormone drugs, agents affecting urinary organs, skeletal muscle relaxants, agents affecting genital organs, antiepileptics, medicine for autonomic nerves, antiparkinsonism agents, diuretics, respiratory stimulants, antimigraine agents, bronchodilating preparations, cardiotonics, coronary vasodilators, peripheral vasodilators, smoking-cessation drugs, agents affecting circulatory organs, antiarrhythmic agents, antitumor agents, antilipemic agents, hypoglycemic agents, antiulcer drugs, cholagogues, prokinetic agents, agents for liver diseases, antiviral drugs, antimotion-sickness agents, antibiotics, agents for habitual intoxication, appetite suppressants, chemotherapeutic drugs, blood coagulation accelerants, anti-Alzheimer disease drugs, serotonin-receptor antagonist antiemetic drugs, gout treatment agents, and mixtures thereof.

Figure 10:
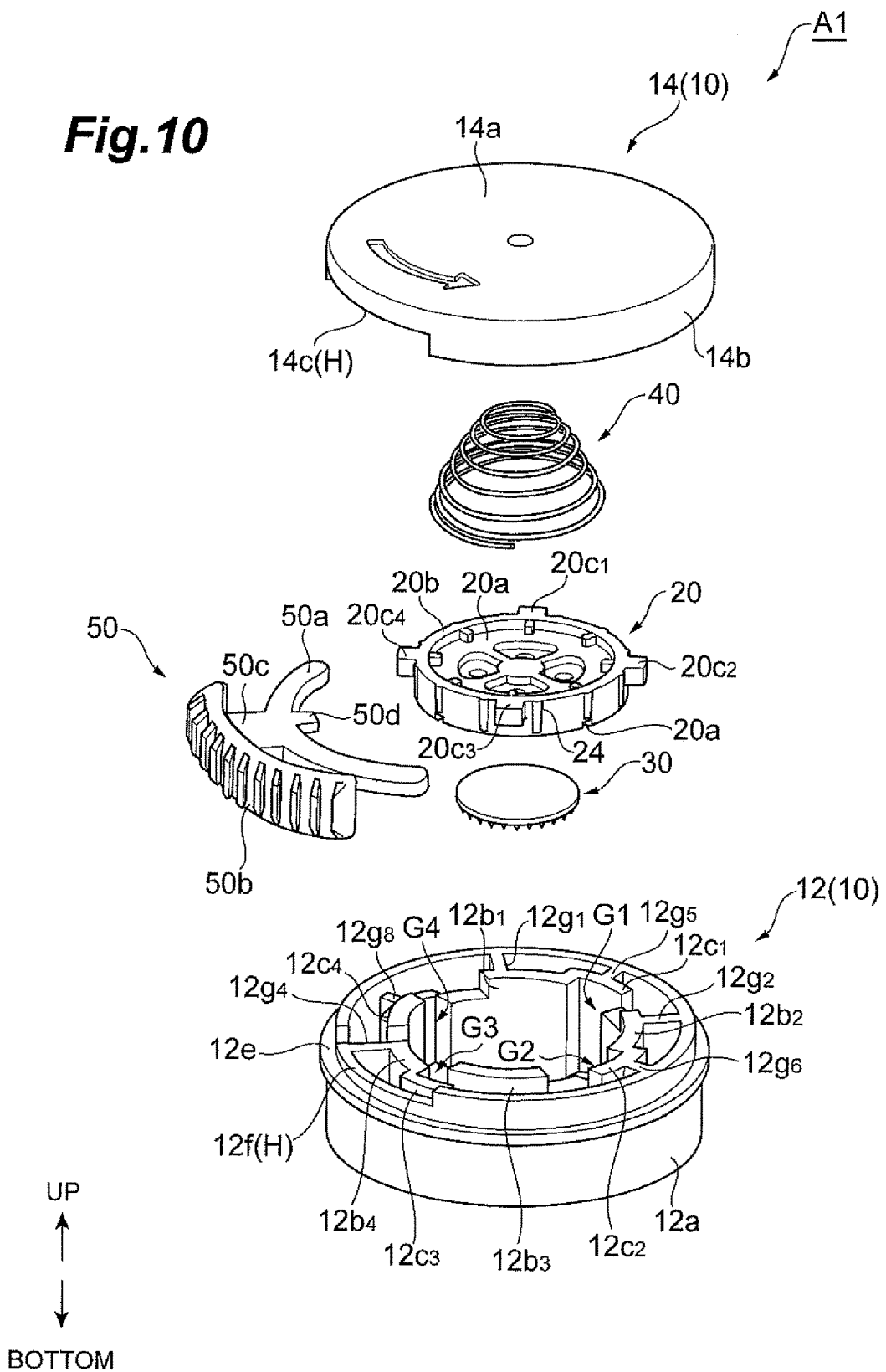
FIG. 10 is an exploded perspective view of the applicator in accordance with the present embodiment.
Figure 22:
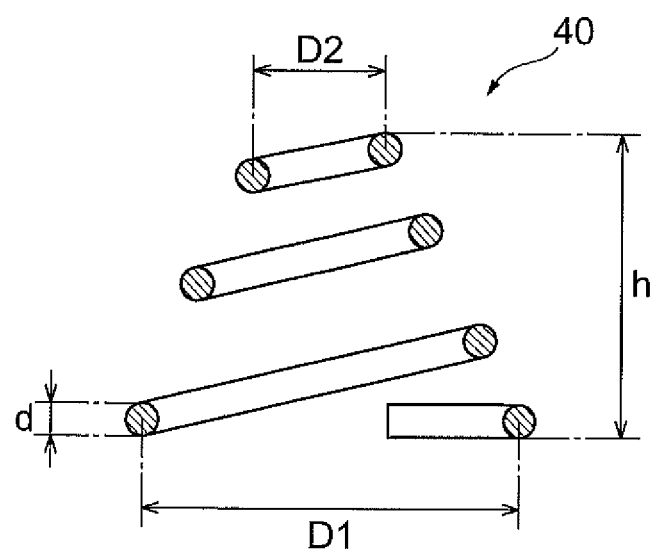
FIG. 22 is a sectional view showing a conical coil spring.

As shown in FIGS. 9 and 10, the conical coil spring 40 is housed in the main body part 12. Specifically, the conical coil spring 40 is arranged between the piston plate 20 and the cover part 14, and is sandwiched between the upper surface of the piston plate 20 and the lower surface of the cover part 14. As shown in FIGS. 9, 10, and 22, the conical coil spring 40 is formed by winding a metal wire having a circular shape in cross section in a spiral manner, and the conical coil spring 40 has a circular cone shape when viewed from its lateral. In the present embodiment, the conical coil spring 40 does not overlap when viewed in the central line direction of the conical coil spring 40. Examples of the metal wire include a stainless steel wire, a piano wire (iron wire), and a copper wire. Among these wires, particularly the stainless steel wire is extremely resistant to corrosion.

In the present embodiment, the smaller diameter side of the conical coil spring 40 is in contact with the cover part 14, and the larger diameter side of the conical coil spring 40 is in contact with the piston plate 20. Parameters concerning the energy of the piston plate 20 actuated by the biasing force of the conical coil spring 40 include: the modulus of transverse elasticity; the wire diameter (d in FIG. 22); the maximum diameter (D1 in FIG. 22); the minimum diameter (D2 in FIG. 22); the total number of coil turns; the weight of the conical coil spring 40; the total weight of the piston plate 20 and the microneedle array 30; the free height (h in FIG. 22); the height in a close contact state; the pitch angle; and the pitch.

As shown in FIGS. 9 to 11, and 23, the release member 50 includes: an interior part 50a located inside of the main body part 12; an exterior part 50b located outside of the main body part 12; and a coupling part 50c that couples the interior part 50a and the exterior part 50b to each other. The interior part 50a is a flat plate having a circular arc-like shape. The diameter of the interior part 50a is larger than the diameter of the interior inner walls $12b_1$ to $12b_4$, and is smaller than the diameter of the outer wall 12a. In the completed state of the applicator A, the interior part 50a is located between the outer wall 12a and the interior inner walls $12b_1$ to $12b_4$ (see FIG. 11). In the completed state of the applicator A, the interior part 50a is placed above the exterior inner walls $12c_3$ and $12c_4$ each having a small height and the coupling walls $12g_3$, $12g_4$, $12g_7$, and $12g_8$ each having a small height (see FIG. 11).

The interior part 50a is integrally provided with a protrusion part 50d that protrudes in the radial direction from the inner edge of the interior part 50a toward the central axis. The protrusion part 50d is a flat plate having a rectangular shape. In the completed state of the applicator A, the protrusion part 50d is located on the circumference having the same radius as that of the interior inner walls $12b_1$ to $12b_4$ and between the first portion $12b_{31}$ of the interior inner wall $12b_3$ and the first portion $12b_{41}$ of the interior inner wall $12b_4$ (see FIG. 11).

Figure 23:
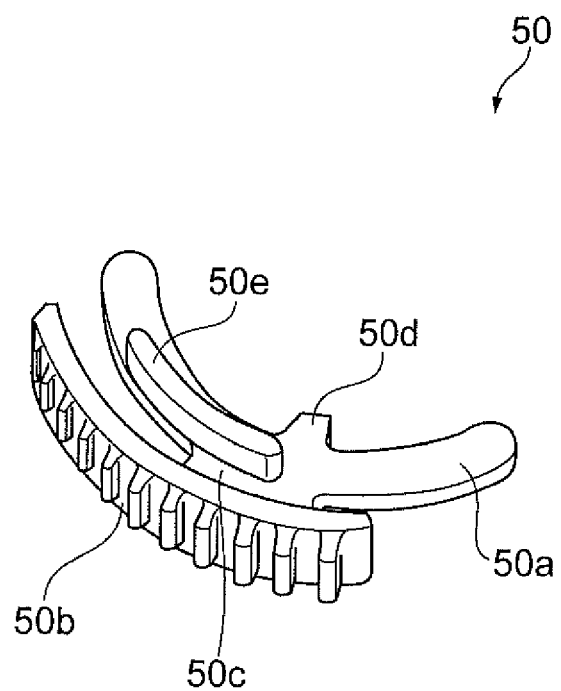
FIG. 23 is a perspective view showing a lower surface side of a release member.

As shown in FIGS. 9 and 23, the interior part 50a is integrally provided with an elongated protrusion 50e that protrudes downward from the lower surface of the interior part 50a. The elongated protrusion 50e has a circular arc-like shape with a curvature equivalent to that of the interior part 50a, and extends along the interior part 50a. In the completed state of the applicator A, the elongated protrusion 50e is located between the exterior inner wall $12c_3$ and the outer wall 12a. In order not to prevent movement in the circumferential direction of the release member 50 to be described later, it is preferable that the height of the elongated protrusion 50e be set to be smaller than the depth of a recessed part formed by the exterior inner wall $12c_3$, the coupling wall $12g_7$, and the outer wall 12a.

Figure 11:
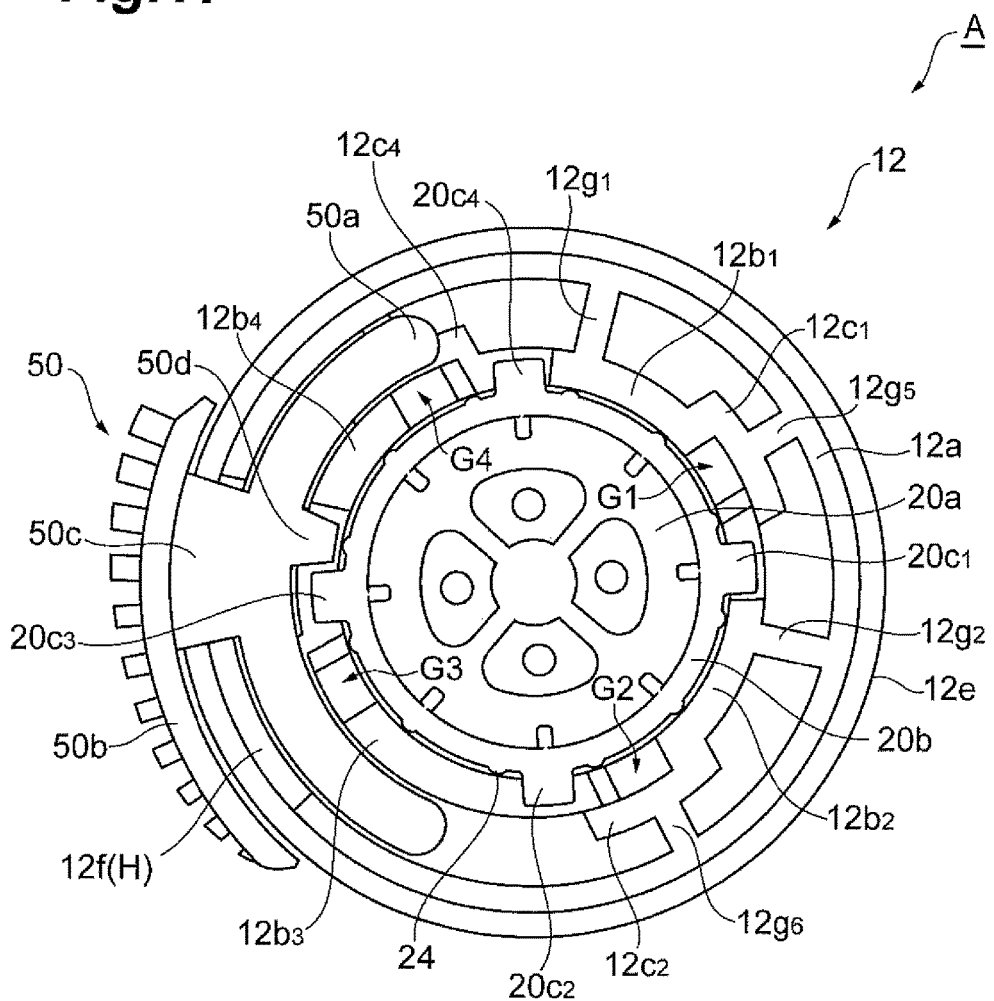
FIG. 11 is a top view showing a state before operation of the applicator in accordance with the present embodiment while a cover part is detached.
Figure 12:
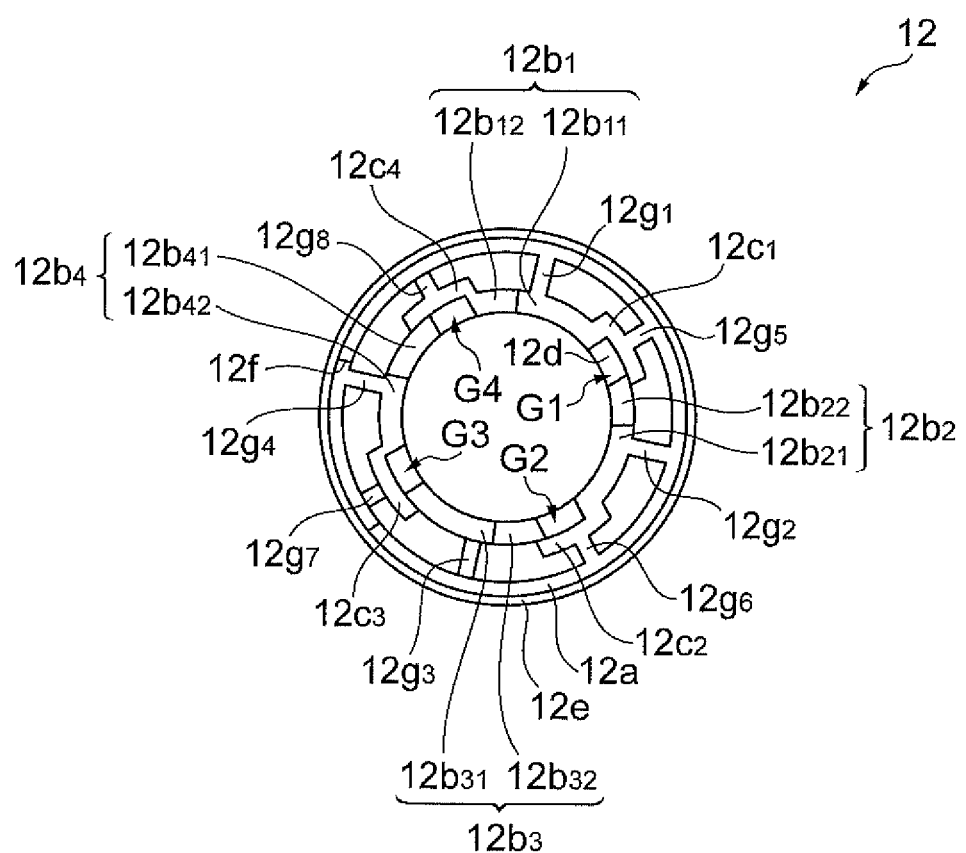
FIG. 12 is a top view showing a main body part.

As shown in FIGS. 10, 11, and 23, the exterior part 50b is a curved plate that extends in the circumferential direction along the outer circumferential surface of the main body part 12, and has a circular arc-like shape in cross section. A plurality of elongated protrusions that extend along the top-bottom direction are provided on the outer surface of the exterior part 50b. The plurality of elongated protrusions are arranged side by side along the circumferential direction. Thus, the outer circumferential surface of the exterior part 50b has irregularities in the circumferential direction. Accordingly, when the user of the applicator A moves the release member 50 in the circumferential direction by touching the outer circumferential surface of the exterior part 50b with user's fingers, the fingers slip less easily on the outer circumferential surface of the exterior part 50b. In order to obtain such an antislip effect, for example, the outer circumferential surface of the exterior part 50b may be embossed or roughened instead of providing the plurality of elongated protrusions. The outer circumferential surface of the exterior part 50b does not particularly need to be processed.

The coupling part 50c is a flat plate having a rectangular shape. The coupling part 50c protrudes in the radial direction from the outer edge of the interior part 50a toward the opposite side to the central axis. In the completed state of the applicator A, the coupling part 50c is exposed on the outer circumferential surface of the main body part 12 through the through-hole H. In order to make the coupling part 50c (release member 50) movable in the extending direction of the through-hole H, the width of the coupling part 50c is set to be smaller than the opening width of the through-hole H.

[2] Method of Manufacturing Applicator

Now, the method of manufacturing the applicator A is described. First, the respective components (the casing 10, the piston plate 20, the microneedle array 30, the conical coil spring 40, and the release member 50) of the applicator A described above are prepared. The coating C is applied in advance to the microneedles 32 of the prepared microneedle array 30. Next, the microneedle array 30 is attached to the lower surface of the piston plate 20.

Subsequently, the interior part 50a of the release member 50 is placed above the exterior inner walls $12c_3$ and $12c_4$ and the coupling walls $12g_3$, $12g_4$, $12g_7$, and $12g_8$ such that the protrusion part 50d of the release member 50 is located above the first portion $12b_{41}$ of the interior inner wall $12b_4$ (see FIG. 11). Accordingly, the release member 50 (coupling part 50c) is located on one end side of the through-hole H.

Subsequently, the piston plate 20 is placed in the main body part 12 such that: the protrusion $20c_1$ of the piston plate 20 is located above the second portion $12b_{22}$ of the interior inner wall $12b_2$; the protrusion $20c_2$ of the piston plate 20 is located above the second portion $12b_{32}$ of the interior inner wall $12b_3$; the protrusion $20c_3$ of the piston plate 20 is located above the second portion $12b_{42}$ of the interior inner wall $12b_4$ and between the protrusion part 50d of the release member 50 and the groove part G3; and the protrusion $20c_4$ of the piston plate 20 is located above the second portion $12b_{12}$ of the interior inner wall $12b_1$ (see FIG. 11). On this occasion, the protrusion part 50d of the release member 50 and the protrusion $20c_4$ of the piston plate 20 are placed above the second portion $12b_{42}$ of the interior inner wall $12b_4$, and hence it is preferable that the width of the second portion $12b_{42}$ be larger than the sum of the width of the protrusion part 50d and the width of the protrusion $20c_4$.

Subsequently, the conical coil spring 40 is placed on the upper surface of the piston plate 20 such that: the larger diameter side of the conical coil spring 40 faces downward; and the smaller diameter side thereof faces upward. In this way, the conical coil spring 40 stably stands up at the time of placing the conical coil spring 40 on the piston plate 20, and hence the applicator A1 can be manufactured more easily.

Subsequently, the cover part 14 is attached to the main body part 12 such that the cutout part 12f of the main body part 12 and the cutout part 14c of the cover part 14 coincide with each other. On this occasion, because the protrusions $20c_1$ to $20c_4$ are placed on the second portions $12b_{12}$ to $12b_{42}$ of the interior inner walls $12b_1$ to $12b_4$, respectively, even if the conical coil spring 40 is compressed by attaching the cover part 14 to the main body part 12, the piston plate 20 is not pushed out in the bottom direction by the conical coil spring 40. That is, the piston plate 20 is locked with the casing 10 (main body part 12). Accordingly, as shown in FIG. 9, the piston plate 20 is held at its retraction position on the cover part 14 side inside of the main body part 12, in the state where the cover part 14 and the piston plate 20 compress the conical coil spring 40. Such a state as described above where the piston plate 20 is locked with the casing 10 (main body part 12) and where the cover part 14 and the piston plate 20 compress the conical coil spring 40 is hereinafter referred to as "locked state".

Locking the piston plate 20 with the casing 10 (main body part 12) at its retraction position as described above is also referred to as cocking. In the present exemplary embodiment, the metal wire that forms the conical coil spring 40 does not overlap when viewed in the central line direction of the conical coil spring 40, and hence the height of the conical coil spring 40 sandwiched between the piston plate 20 and the cover part 14 becomes equivalent to the wire diameter, in the state where the piston plate 20 is locked (cocked) with the casing 10 (see FIG. 9).

Through the above-mentioned procedures, assembling of the applicator A is completed. Accordingly, the conical coil spring 40 remains in a compressed state until the applicator A is used by a user after manufacture and shipping thereof.

[3] Method of Using Applicator

Figure 24:
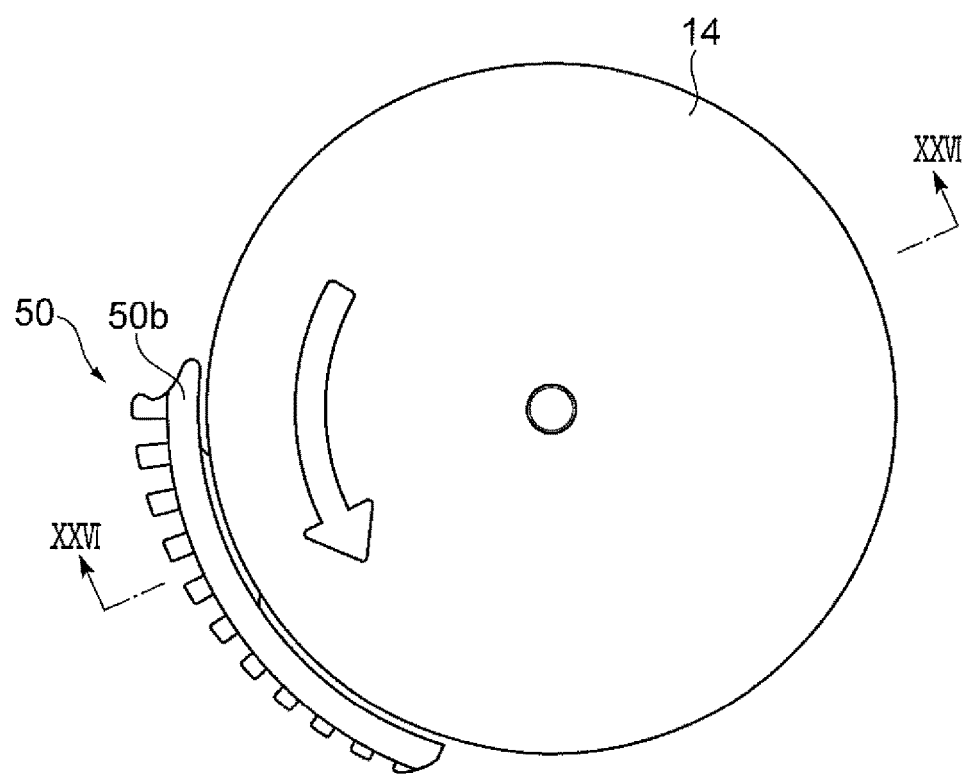
FIG. 24 is a sectional view showing a state after operation of the applicator in accordance with the present embodiment.

Now, the method of using the applicator A is described. First, the applicator A is positioned with respect to a portion of skin to which a medical agent or the like is desired to be applied, such that the microneedles 32 face the skin. The release member 50 is slid to another end side of the through-hole H while the applicator A is kept positioned (see FIG. 24). As a result, the protrusion part 50d of the release member 50 pushes the protrusion $20c_3$ of the piston plate 20 toward the groove part G3. Consequently, the piston plate 20 turns.

Figure 25:
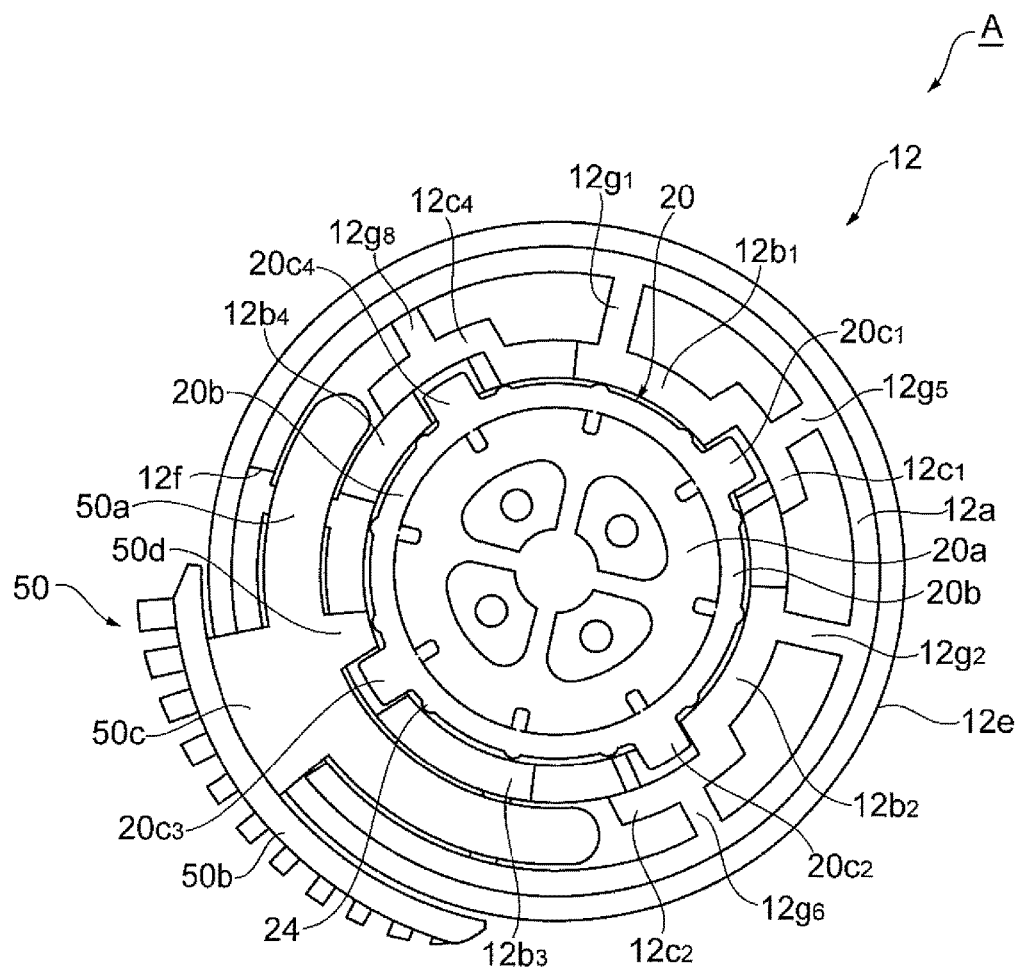
FIG. 25 is a top view showing the state after operation of the applicator in accordance with the present embodiment while the cover part is detached.
Figure 26:
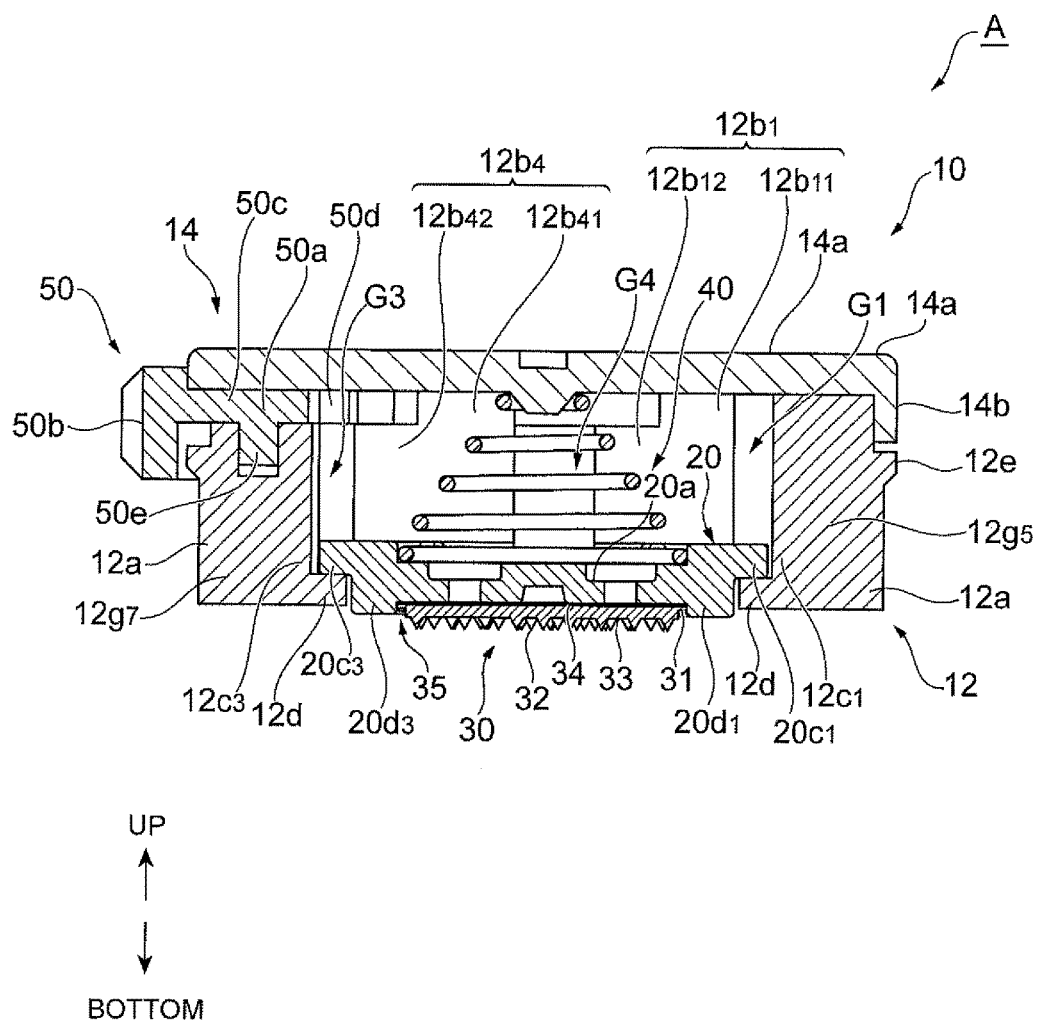
FIG. 26 is a sectional view taken along line XXVI-XXVI in FIG. 24.

The upper end of the second portion $12b_{22}$ is adjacent to the end part on the cover part 14 side of the groove part G1 (the upper end part of the groove part G1). Hence, if the piston plate 20 turns, the protrusion $20c_1$ slides on the upper end of the second portion $12b_{22}$ to reach the groove part G1. The upper end of the second portion $12b_{32}$ is adjacent to the end part on the cover part 14 side of the groove part G2 (the upper end part of the groove part G2). Hence, if the piston plate 20 turns, the protrusion $20c_2$ slides on the upper end of the second portion $12b_{32}$ to reach the groove part G2. The upper end of the second portion $12b_{42}$ is adjacent to the end part on the cover part 14 side of the groove part G3 (the upper end part of the groove part G3). Hence, if the piston plate 20 turns, the protrusion $20c_3$ slides on the upper end of the second portion $12b_{32}$ to reach the groove part G3. The upper end of the second portion $12b_{12}$ is adjacent to the end part on the cover part 14 side of the groove part G4 (the upper end part of the groove part G4). Hence, if the piston plate 20 turns, the protrusion $20c_4$ slides on the upper end of the second portion $12b_{12}$ to reach the groove part G4. As a result, the locking (cocking) of the piston plate 20 with the casing 10 (main body part 12) is released (see FIG. 25). Then, the piston plate 20 is moved by the biasing force (elastic force) of the conical coil spring 40 outward (toward the skin) along the groove parts G1 to G4 (the central axis of the main body part 12) inside of the main body part 12, and the microneedle array 30 collides against the skin S (see FIG. 26 and (a) of FIG. 27). At this time, the protrusions $20c_1$ to $20c_4$ are brought into contact with the bottom wall 12d, and hence the piston plate 20 is prevented from jumping out of the casing 10 (main body part 12).

When the microneedle array 30 collides against the skin S, the microneedles 32 are stuck into the skin S. The speed of the microneedles 32 (piston plate 20) on this occasion may be 4 m/s to 30 m/s, 4 m/s to 15 m/s, or 7 m/s to 15 m/s. In the configuration in which the microneedles 32 collide against the skin S at a speed of 4 m/s to 30 m/s, the microneedles 32 can be appropriately stuck into the skin S, whereby the medical agent or the like can be sufficiently transferred into the body of an animal.

[4] Actions of Present Embodiment

Unlike the piston plate 20 of the present embodiment, when a piston plate 200 without the protrusion parts $20d_1$ to $20d_4$ is used to allow the microneedle array 30 to collide against the skin S, the skin S may be greatly recessed by the microneedle array 30 (see (a) of FIG. 27). This may cause the microneedle array 30 to bounce off the skin S due to elastic force of the skin S. Then, the microneedles 32 once stuck into the skin may come off the skin S to affect transfer of the active ingredients into a body. The (a) of FIG. 27 shows a state when the piston plate 200 without the protrusion parts $20d_1$ to $20d_4$ on the lower surface (the surface opposite to the upper surface) of the main body 20a collides against the skin S.

In the present embodiment, the protrusion parts $20d_1$ to $20d_4$ are arranged in the periphery of the protrusion part 33 while being spaced apart from the protrusion part 33. Thus, even if the protrusion part 33 collides against the skin S to cause the skin S to undulate (even if undulation is produced in the skin), the undulation is reduced by the protrusion parts $20d_1$ to $20d_4$ (see (b) of FIG. 27). This causes the piston plate 20 not to easily bounce off the skin S, and thus the microneedles once stuck into the skin S tends to easily stay in the skin S. As a result, the active ingredients can be sufficiently transferred into a body. The (b) of FIG. 27 shows a state when the piston plate 20 in accordance with the present embodiment collides against the skin S.

In the present embodiment, a portion between the protrusion part 33 and the protrusion parts $20d_1$ to $20d_4$ forms a recessed part 35 recessed from surfaces of the protrusion parts $20d_1$ to $20d_4$ and the protrusion part 33. In this case, undulation (transmission of vibration) of the skin S may be absorbed in the recessed part 35. Accordingly, a bounce of the piston plate 20 from the skin S can be reduced further. It is conjectured that pressing the protrusion parts $20d_1$ to $20d_4$ on the skin allows mechanical energy applied by the applicator A to form nodes of vibration so that a vibrating surface between the nodes absorbs vibration energy in a part of the skin surrounded by the protrusion parts $20d_1$ to $20d_4$ (a region of the skin corresponding to the recessed part 35 and the microneedle region).

In the present embodiment, a user can make a puncture in skin S using the applicator A by simply sliding the release member 50. Accordingly, whoever may use the applicator A, the biasing force of the conical coil spring 40 is transmitted to the microneedles 32 with the intermediation of the piston plate 20, and the microneedles 32 are stuck into the skin S with a given impact force. Hence, the puncture in the skin S can be reliably made (the reproducibility of the puncture is enhanced). When the microneedles 32 are stuck into the skin S, active ingredients of the coating C that adhere to the microneedles 32 are delivered into the body, and the active ingredients are transferred into the body through the skin S.

In the applicator A in accordance with the present embodiment, the locked state where the piston plate 20 is locked with the casing 10 is released by the release member 50. Consequently, the biasing force of the conical coil spring 40 acts on the piston plate 20, and the piston plate 20 moves along the groove parts G1 to G4 inside of the main body part 12 to reach a position for action on the skin S. Thus, a member such as a shaft that extends in the axial direction of the main body part 12 (the height direction of the applicator A) does not need to be attached to the piston plate 20. Further, in the applicator A in accordance with the present embodiment, the conical coil spring 40 is used to exert biasing force on the piston plate 20. When being compressed, the height of the conical coil spring 40 becomes extremely smaller compared with general cylindrical coil springs. In this way, the height of the applicator A itself can be made smaller, thereby achieving a reduction in weight of the applicator A.

Depending on the type of a medical agent or the like, the applicator A needs to be held on the skin S for a long time after a collision of the microneedles 32 against the skin S. Even in such a case, with the use of the applicator A in accordance with the present embodiment that can achieve a reduction in size and weight, the user can put on clothing and move without any restriction with the applicator A being attached to the skin S. Moreover, because the applicator A in accordance with the present embodiment is small, even in the case where the user freely moves in such a manner, the applicator A is extremely unlikely to collide against another object (obstacle) to thereby cause the microneedles 32 to come off the skin S or to break and stay in the skin S.

In the case where a conventional large-sized applicator is used, the user may have trouble handling it or feel fear due to the large appearance thereof. In contrast, the applicator A in accordance with the present embodiment that can achieve a reduction in size and weight can be easily handled, and a feeling of fear that the user may develop can be significantly reduced.

In the applicator A in accordance with the present embodiment, the release member 50 is located lateral to (on the outer circumferential surface of) the casing 10 (main body part 12), and hence the release member 50 is suppressed from extending in the axial direction of the main body part 12 (the height direction of the applicator A). Thus, the height of the applicator A itself can be made further smaller.

[5] Other Embodiments

Hereinabove, embodiments of the present invention have been described in detail, but the present invention is not limited to the above-mentioned embodiments. For example, as shown in FIG. 28 or 29, an adhesive substance 60 with adhesive capability may be provided in at least a part of a surface of each of the protrusion parts $20d_1$ to $20d_4$. The adhesive substance 60, for example, includes acrylic, synthetic rubber, and silicon. FIG. 28 shows a state where the adhesive substance 60 is provided over the entire surface of each of the protrusion parts $20d_1$ to $20d_4$. The (a) of FIG. 28 shows a cross section of the piston plate 20, and the (b) of FIG. 28 shows a bottom surface of the piston plate 20. FIG. 29 shows a state where the adhesive substance 60 is provided in a part of the surfaces of the protrusion parts $20d_1$ to $20d_4$. The (a) of FIG. 29 shows, for each of the protrusion parts $20d_1$ to $20d_4$, a state where the adhesive substance 60 is provided in a part of the surface of the protrusion parts $20d_1$ to $20d_4$. The (b) of FIG. 29 shows a state where the adhesive substance 60 is provided in a part of the surface of at least one of the protrusion parts $20d_1$ to $20d_4$ (the protrusion parts $20d_1$ and $20d_3$ in (b) of FIG. 29). Providing the adhesive substance 60 in the piston plate 20 as described above allows the adhesive substance 60 to tend to adhere to the skin when the piston plate 20 collides against the skin S. Accordingly, a bounce of the piston plate 20 from the skin S can be reduced more.

Figure 30:
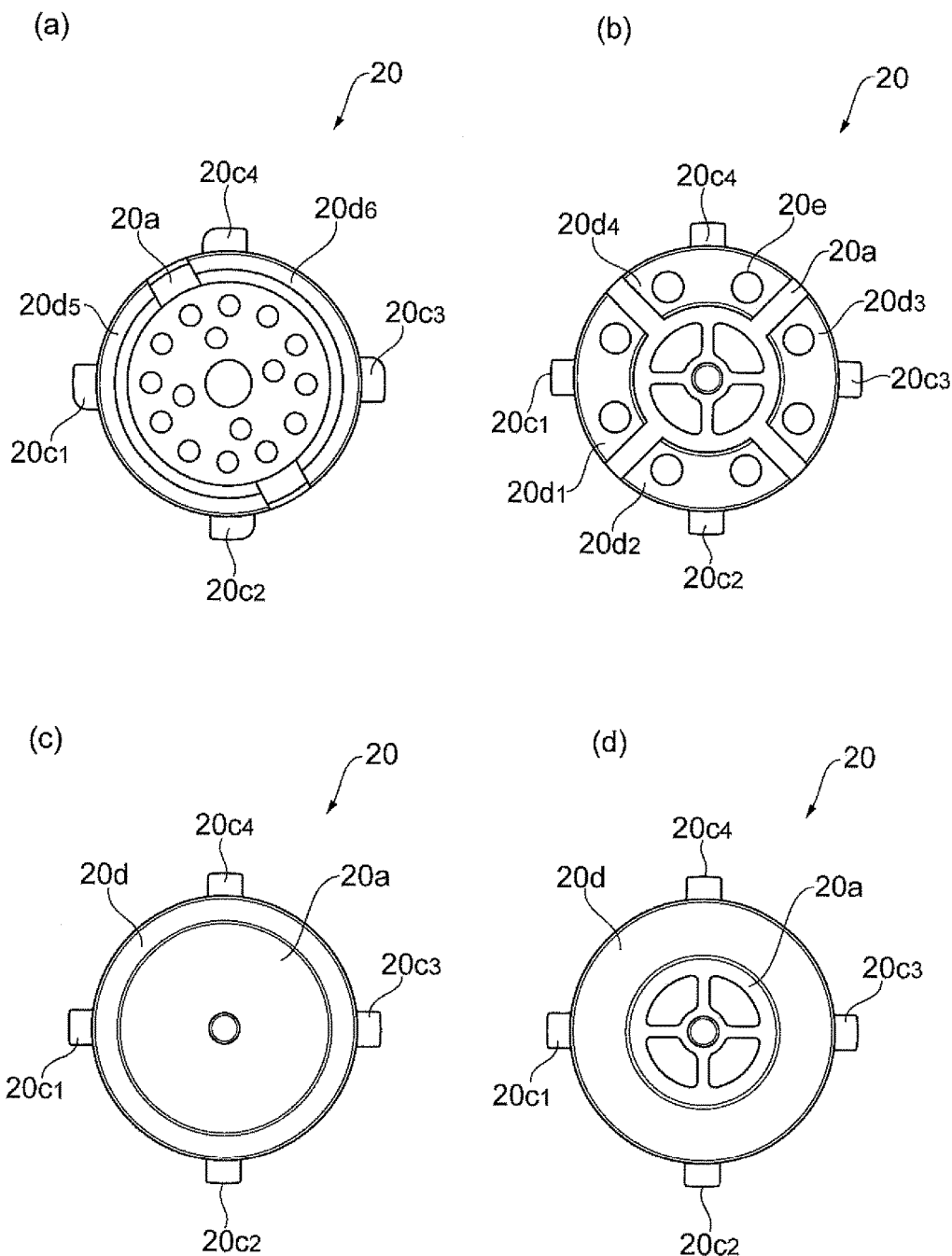
FIG. 30 shows still another example of the piston plate.

In the above-mentioned embodiments, although the piston plate 20 includes the four protrusion parts $20d_1$ to $20d_4$, the piston plate 20 may include at least one protrusion part as shown in FIG. 30. The (a) of FIG. 30 shows a state where two protrusion parts $20d_5$ and $20d_6$ each having a circular arc-like shape are provided in the lower surface (the surface opposite to the upper surface) of the main body 20a. These protrusion parts $20d_5$ and $20d_6$ face each other and are located on a circumference having the same radius. The (b) of FIG. 30 shows a state where two through-holes 20e are formed in each of the protrusion parts $20d_1$ to $20d_4$. Each of (c) and (d) of FIG. 30 shows a state where one protrusion part 20d having an annular shape is provided in the lower surface (the surface opposite to the upper surface) of the main body 20a. A width of the protrusion part 20d shown in (d) of FIG. 30 is set to be more than a width of the protrusion part shown in (c) of FIG. 30.

Figure 31:
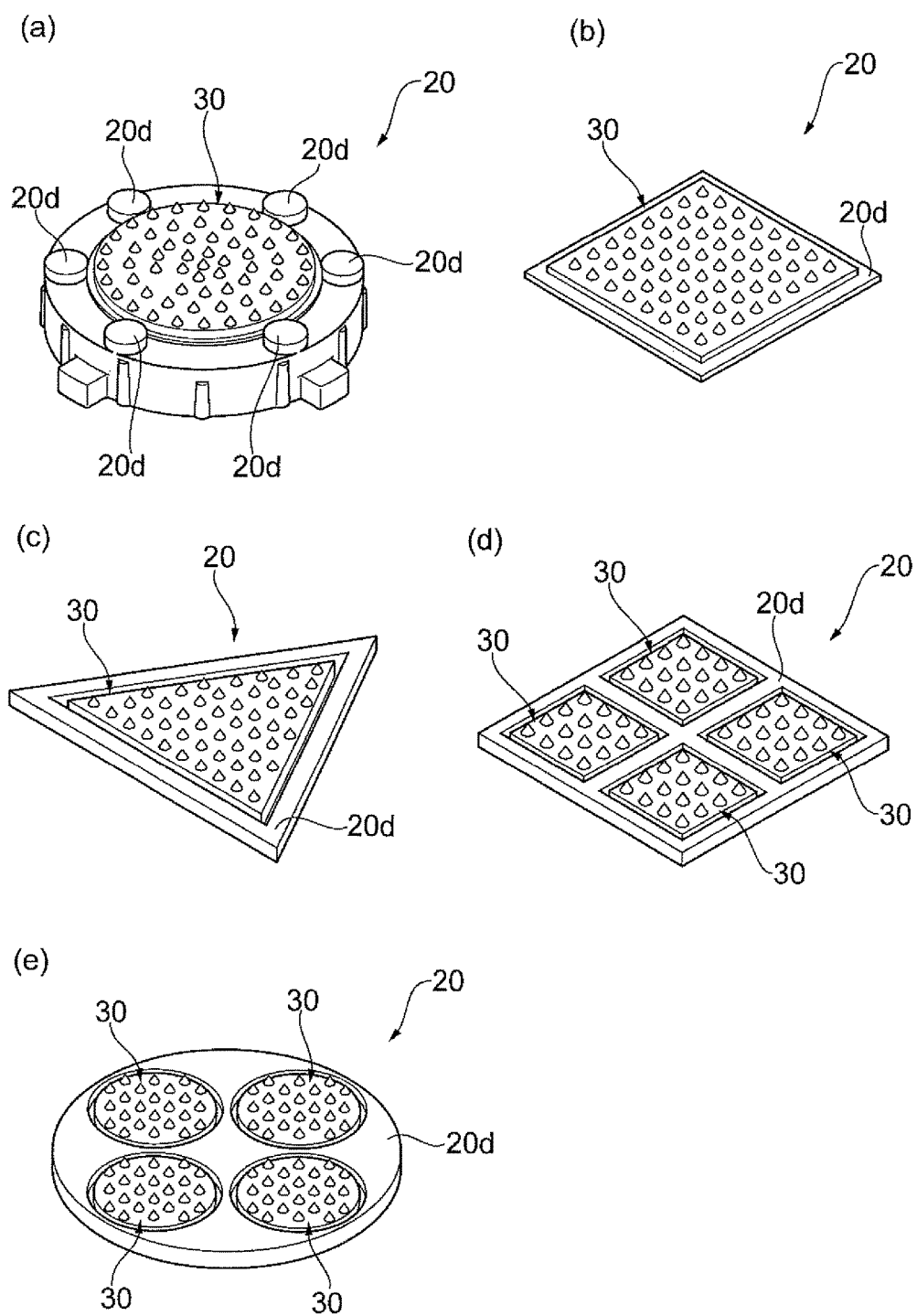
FIG. 31 shows still another example of the piston plate.

Still another form of the piston plate 20 is shown in FIG. 31. The (a) of FIG. 31 shows the piston plate 20 in which a plurality of protrusion parts (six protrusion parts in (a) of FIG. 31) 20d each having a columnar shape are arranged in the lower surface of the main body 20a so as to surround the microneedle array 30 at predetermined intervals. The (b) and (c) of FIG. 31 show states where outlines of the piston plate 20 having a quadrangular shape and a triangular shape, respectively. As above, the outline of the piston plate 20 is not limited to a circular shape, and thus can be formed in a variety of shapes other than the circular shape. In this case, a shape of the protrusion part 20d may correspond to the outline of the piston plate 20, or may be different from the outline of the piston plate 20. In addition, an outline of the microneedle array 30 may correspond to a shape of the protrusion part 20d surrounding the microneedle array 30, or may be different from the shape of the protrusion part 20d surrounding the microneedle array 30. Each of (d) and (e) of FIG. 31 shows the piston plate 20 in which a plurality of microneedle arrays 30 can be arranged. In (d) of FIG. 31, the protrusion part 20d having a lattice shape is provided in the lower surface of the main body 20a of the piston plate 20, and four recessed parts in the shape of a rectangle surrounded by the main body 20a and the protrusion part 20d are formed. The microneedle arrays 30 are arranged in each of the recessed parts. The (e) of FIG. 31 shows another variation of (d) of FIG. 31, in which each of recessed parts has a circular shape.

In the above-mentioned embodiments, the piston plate 20 and the microneedle array 30 are integrated with each other, however, the piston plate 20 shown in each of FIGS. 13 to 19 and the microneedle array 30 shown in each of FIGS. 20 and 21 may be separately provided. In the case where the piston plate 20 and the microneedle array 30 are separately provided, the microneedle array 30 is placed on the skin S, the applicator A is placed on the skin S so as to be opposed to the microneedle array 30 and then, the applicator A is actuated. As a result, the piston plate 20 collides against the microneedle array 30 on the skin S, and a puncture into the skin is made. In this case, the applicator A and the microneedle array 30 are arranged to face each other so that the protrusion parts $20d_1$ to $20d_4$ can surround the microneedle array 30 when the piston plate 20 collides against the microneedle array 30 on the skin S.

Figure 32:
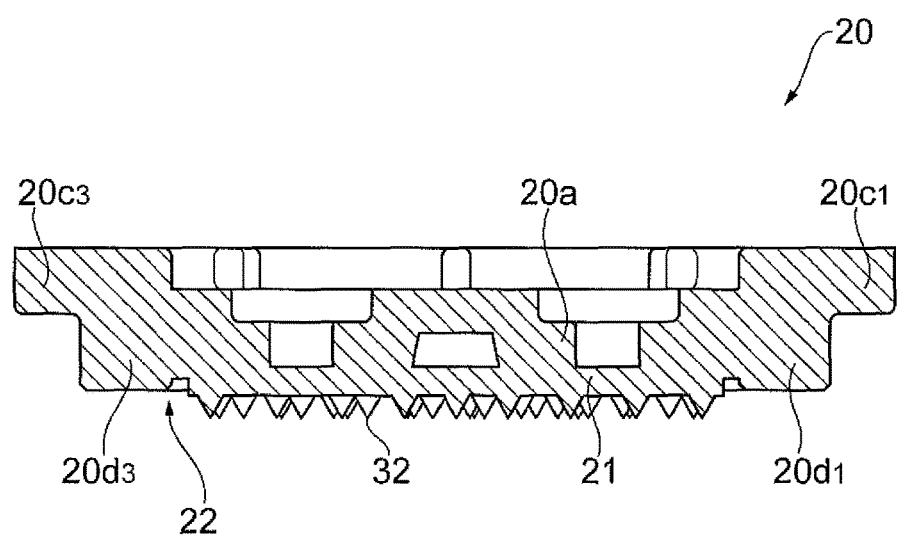
FIG. 32 shows still another example of the piston plate.

In the above-mentioned embodiments, the microneedle array 30 is integrated with the piston plate 20. Alternatively, as shown FIG. 32, the microneedles 32 may be shaped integrally with the lower surface of the piston plate 20. The piston plate 20 includes the protrusion parts $20d_1$ to $20d_4$, and a protrusion part 21. The protrusion part 21 is located inside the protrusion parts $20d_1$ to $20d_4$. That is, the protrusion part 21 is surrounded by the protrusion parts $20d_1$ to $20d_4$. A surface of the protrusion part 21 is located outward from surfaces of the protrusion parts $20d_1$ to $20d_4$. The protrusion part 21 and the protrusion parts $20d_1$ to $20d_4$ are spaced apart from each other. A portion between the protrusion part 21 and the protrusion parts $20d_1$ to $20d_4$ forms a recessed part 22 recessed from surfaces of the protrusion parts $20d_1$ to $20d_4$ and the protrusion part 33. In this case, the main body 20a of the piston plate 20 can be regarded as being equal to the substrate of the microneedle array. That is, the microneedle array can be regarded as behaving as the piston plate 20.

In the above-mentioned embodiments, although the surface of the protrusion part 33 (surface for mounting microneedles) is located outward (downward) from the surfaces of the protrusion parts $20d_1$ to $20d_4$, a positional relationship between the surface of the protrusion part 33 and the surfaces of the protrusion parts $20d_1$ to $20d_4$ is not limited to the above. For example, the surface of the protrusion part 33 and the surfaces of the protrusion parts $20d_1$ to $20d_4$ may be located at a substantially same height, or the surfaces of the protrusion parts $20d_1$ to $20d_4$ may be located outward (downward) from the surface of the protrusion part 33. A leading end of each of the microneedles 32 may be located outward (downward) from the surfaces of the protrusion parts $20d_1$ to $20d_4$ so that the microneedles 32 are stuck into the skin S.

In the above-mentioned embodiments, the microneedles 32 are arranged at substantially regular intervals in a zigzag (alternate) pattern on the surface of the substrate 31. Alternatively, the density of the microneedles 32 on the substrate 31 may be different. For example, the density of the microneedles 32 may be set to be higher in the vicinity of the center of the substrate 31 than in the periphery thereof, and may be set to be higher in the periphery of the substrate 31 than in the vicinity of the center thereof.

The heights of the microneedles 32 may be all the same, and may be different. In the case where the heights of the microneedles 32 are different, for example, the heights of the microneedles 32 may be set to be larger in the vicinity of the center of the substrate than in the periphery thereof, and may be set to be larger in the periphery of the substrate than in the vicinity of the center thereof.

As shown in (a) of FIG. 33, it is allowed to use a conical coil spring 41 having both end parts that are each shaved to be flat along a virtual plane orthogonal to the central line of the conical coil spring 41. An end on the smaller diameter side of the conical coil spring 41 is brought into contact with a partition wall 10a, and an end on the larger diameter side of the conical coil spring 41 is brought into contact with the piston plate 20. Thus, if the conical coil spring 41 is configured as described above, the contact area of the conical coil spring 41 with each of the partition wall 10a and the piston plate 20 can be made larger. Accordingly, the conical coil spring 41 can be stably arranged inside of the casing 10.

In the above-mentioned embodiments, the conical coil spring 40 is used to exert a biasing force on a piston P, but a non-linear coil spring having another shape may be used. Examples of the non-linear coil spring having another shape include a coil spring 42 having a drum-like shape with a narrow part (see (b) of FIG. 33), and a coil spring 43 having a barrel-like shape (see (c) of FIG. 33). Alternatively, a cylindrical coil spring 44 shown in (d) of FIG. 33 may be used.

In the above-mentioned embodiments, the metal wire that forms the conical coil spring 40 does not overlap when viewed in the extending direction of the central line of the conical coil spring 40. Alternatively, it is possible to use the conical coil spring 40 formed by winding a metal wire such that the metal wire overlaps when viewed in the extending direction of the central line thereof. In both of the cases, the free height h of the conical coil spring 40 can be set to be smaller than a value obtained by multiplying the wire diameter d by the total number of turns.

In the above-mentioned embodiments, the locking (cocking) of the piston plate with the casing (main body part) is released by exerting a turning force on the piston plate, or by turning the piston plate. However, the force that is exerted on the piston plate for releasing the locking of the piston plate is not limited to the turning force. For example, the locking of the piston plate may be released by moving the piston plate in the horizontal direction with respect to the casing (main body part). Alternatively, the locking of the piston plate may be released by moving or turning a lock member in the horizontal direction without moving the piston plate that is locked with the casing (main body part) with the intermediation of the lock member.

Figure 34:
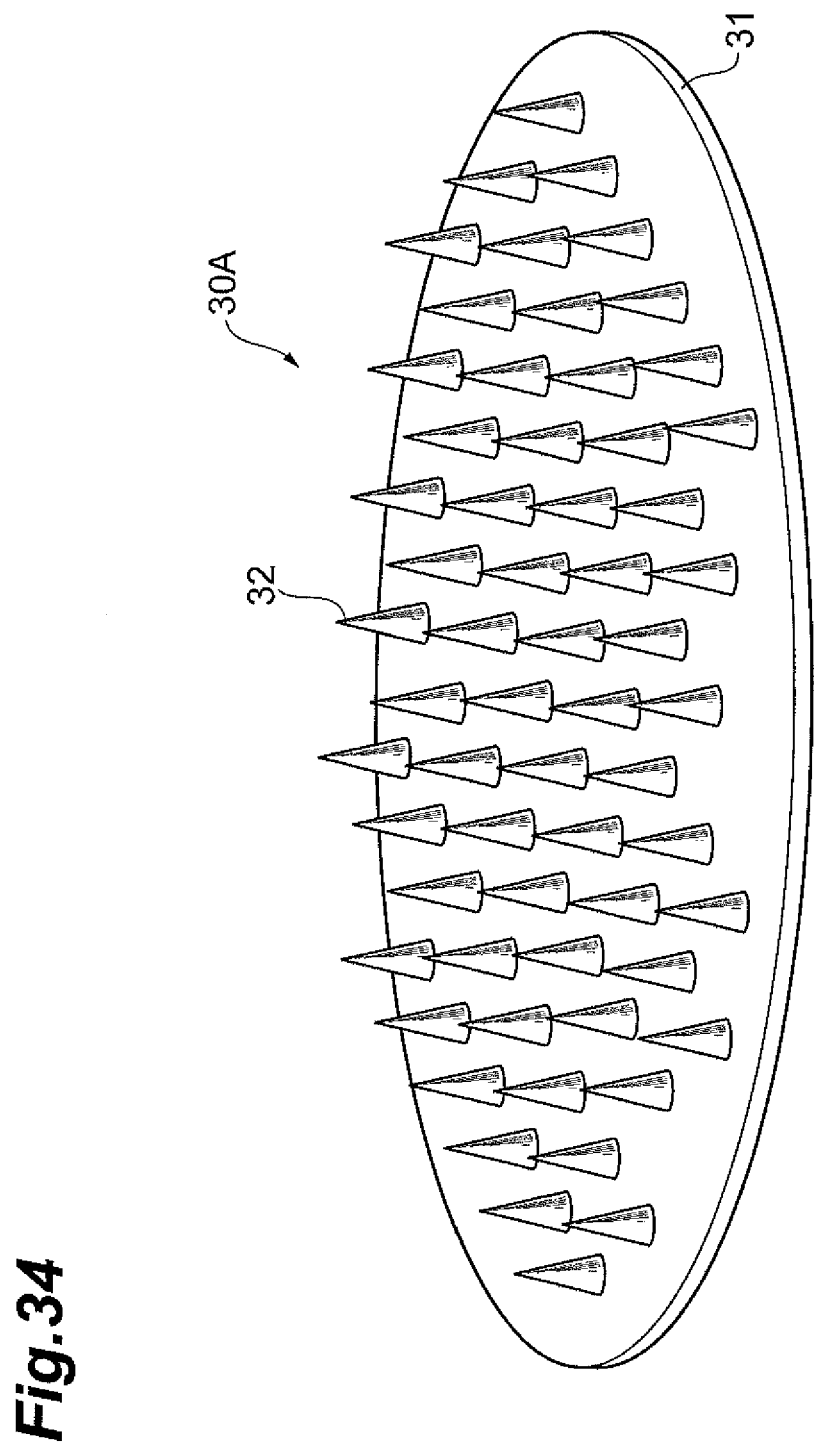
FIG. 34 is a perspective view partially showing a microneedle array in accordance with a variation.

Although the microneedle array 30 includes the protrusion part 33 in the above-mentioned embodiments, the present invention is also applicable in the case of using a microneedle array 30A without a protrusion part shown in FIG. 34. The microneedle array 30A includes a disc-like substrate 31, and a plurality of microneedles 32 that are provided on a surface of the substrate 31. As with the above-mentioned embodiments, an outer diameter of the substrate 31 is set to be equivalent to or slightly smaller than an inner diameter of a circle formed by the protrusion parts $20d_1$ to $20d_4$. Thus, the microneedle array 30A is arranged inside the protrusion parts $20d_1$ to $20d_4$. The substrate 31 and the protrusion parts $20d_1$ to $20d_4$ may be spaced apart from each other to allow a portion between the surface (surface for mounting microneedles) of the substrate 31, including the microneedles 32, and the protrusion parts $20d_1$ to $20d_4$ to form recessed parts that are recessed from both of the surface of the substrate 31 and the surfaces of the protrusion parts $20d_1$ to $20d_4$.

The microneedle array 30A is attached to the lower surface of the main body 20a of the piston plate 20 to be integrated with the piston plate 20. Length of needles of the microneedle array 30A may be set so that leading ends of the microneedles 32 project downward from the protrusion parts $20d_1$ to $20d_4$. The applicator to which the microneedle array 30A is attached is actuated so that when the microneedles 32 are stuck into skin, at least a part of the surface of the substrate 31, including the microneedles 32, can collide against the skin.

A portion in the lower surface (main surface) of the main body 20a of the piston plate 20, where the microneedle array 30A is attached, is a microneedle region where the microneedles 32 are located. In this variation, the microneedles 32 are not directly provided in the lower surface of the main body 20a, but the microneedle array 30A including the microneedles 32 is attached to the lower surface of the main body 20a of the piston plate 20. Thus, the microneedle region in this variation is a region where the microneedles 32 are indirectly arranged in the piston plate 20.

The microneedles may be provided on the lower surface (main surface) of the main body of the piston plate, or the piston plate itself, without preparing the microneedle array. The microneedle region in this variation is a region where the microneedles 32 are directly arranged on the main surface of the piston plate. Even in this variation, a portion between the microneedle region and the protrusion parts (corresponding to the protrusion parts $20d_1$ to $20d_4$ in the above-mentioned embodiments) may form recessed parts that are recessed from both of the microneedle region and surfaces of the protrusion parts.

The microneedle array 30A and the piston plate 20 may be separated from each other. In this case, the microneedle array 30A is placed on skin, the applicator A is placed on the skin so as to be opposed to the microneedle array 30 and then, the applicator A is actuated. As a result, the piston plate 20 collides against the microneedle array 30A on the skin S, and a puncture into the skin S is made. In this case, the applicator A and the microneedle array 30A are arranged to face each other so that the protrusion parts $20d_1$ to $20d_4$ can surround the microneedle array 30A when the piston plate 20 collides against the microneedle array 30A on the skin S.

Even if the microneedle array 30A is substituted for the microneedle array 30, the same effect as that of the above-mentioned embodiments can be acquired.

A sectional shape of each of the protrusion part $20d_1$ to $20d_4$ taken along a radial direction of the piston plate 20 is not limited, and thus, for example, includes a rectangle, a circle, an ellipse, a semicircle, a triangle, and other polygons. The protrusion parts $20d_1$ to $20d_4$ may be formed softer than other portions in the piston plate 20, and thus, for example, the protrusion parts $20d_1$ to $20d_4$ may be made from material softer than that of other portions in the piston plate 20. The protrusion parts $20d_1$ to $20d_4$ may be used not only to improve puncture performance, but also to, for example, allow the protrusion parts or an assembly of the protrusion parts and another component to secure sterility of the microneedles.

A difference in height (a difference D in height shown in FIG. 36) between a leading end surface of the protrusion part of the piston plate and a leading end of the microneedle may be 0 mm or more than 0 mm. A lower limit of the difference in height, for example, may be 0 mm, 0.1 mm, 0.2 mm, 0.3 mm, 0.4 mm, 0.5 mm, 0.6 mm, 0.7 mm, 0.8 mm, 0.9 mm, or 1 mm. An upper limit of the difference in height, for example, may be 10 mm, 9 mm, 8 mm, 7 mm, 6 mm, 5 mm, 4 mm, 3 mm, 2 mm, 1.9 mm, 1.8 mm, 1.7 mm, 1.6 mm, 1.5 mm, 1.4 mm, 1.3 mm, 1.2 mm, 1.1 mm, 1.0 mm, 0.9 mm, 0.8 mm, 0.7 mm, 0.6 mm, or 0.5 mm. The difference in height more than 0 mm is premised on the leading end of the microneedle that projects outward (downward) from the leading end surface of the protrusion part of the piston plate when the applicator is viewed from sides. Setting the difference in height in this way enables improving puncture performance.

Where the difference in height is indicated as D, and an average length of the microneedles is indicated as F (see length F shown in FIG. 36), a lower limit of a value obtained by D/F, which is referred to as a "value D/F" or a "D/F ratio" in the present specification, for example, may be 0.0, 0.1, 0.2, 0.3, 0.4, 0.5, 0.6, 0.7, 0.8, 0.9, or 1.0. An upper limit of the value D/F, for example, may be 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, or 1.0. Setting the value D/F indicating a ratio of the difference in height to the average length of the microneedles in this way enables improving puncture performance.

EXAMPLES

Hereinafter, the present invention is described more specifically by way of an example, but the present invention is not limited to the following example.

Puncture performance was evaluated by using: the applicator A in accordance with the present embodiment (Example 1); an applicator in which the piston plate 20 of the applicator A is substituted for the form shown in FIG. 28 (Example 2); and an applicator in which the piston plate of the applicator A is substituted for the form shown in (a) of FIG. 27 (comparative example). That is, Example 1 included the piston plate 20 that had the protrusion parts $20d_1$ to $20d_4$. Example 2 had the same structure as that of Example 1 other than that the piston plate 20 had an adhesive substance 60 in addition to the protrusion parts $20d_1$ to $20d_4$. The comparative example had the same structure as that of Example 1 other than that the piston plate 20 did not have the protrusion parts $20d_1$ to $20d_4$ as well as the adhesive substance 60. For the evaluation of the puncture performance, ovalbumin (OVA) was delivered to rabbit skin (in vivo rabbit) using the microneedle array 30, and the transfer rate of OVA to the rabbit skin was obtained. The puncture performance was evaluated on the basis of the transfer rate thus obtained. The transfer rate here refers to the rate of the amount of OVA delivered to the rabbit skin to the amount of OVA (coating C) firmly fixed to the microneedles 32.

In any one of Examples 1 and 2, and the comparative example, a total weight of an actuation part including the piston plate 20, the microneedle array 30, and the conical coil spring 40, was set to 1.2 g.

The prepared microneedle array 30 was made of polylactide. The area of the substrate 31 of the microneedle array 30 was 1.13 cm². The number of the microneedles 32 of the microneedle array 30 was 640. The density of the microneedles 32 of the microneedle array 30 was 566 needles/cm². The height of each microneedle 32 of the microneedle array 30 was 500 μm. The coating range when OVA was applied to the microneedles 32 was a range of about 180 μm including the tips of the microneedles 32. The initial content of OVA coating the microneedles 32 was 80 μg.

Figure 35:
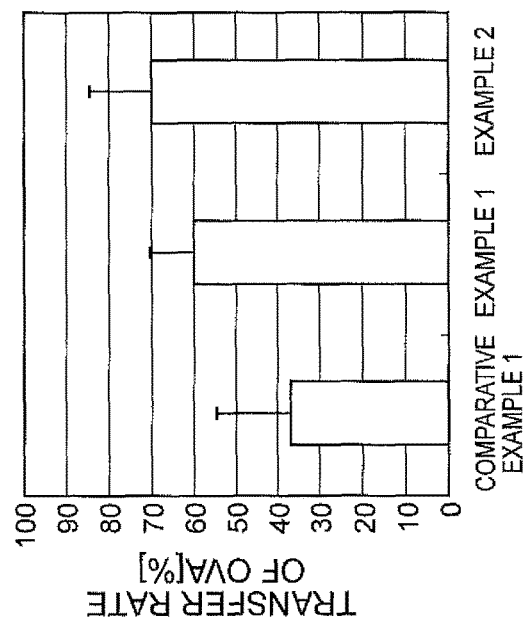
FIG. 35 is an illustration for describing examples.

The applicators each were placed still on the rabbit skin, and the microneedles 32 were stuck into the rabbit skin by actuating the applicators each, whereby OVA was delivered into the rabbit skin. After the delivery of OVA, the microneedle array 30 removed from the rabbit skin was immersed in phosphate buffered saline (PBS), whereby OVA was extracted. The amount of extracted OVA was subtracted from the initial content, whereby the amount of transfer was obtained. The transfer rate was obtained from the ratio of the amount of transfer to the initial content. This kind of administration of OVA into the rabbit skin was repeated three times, and then an average value of the three transfer rates and a standard deviation were calculated. Further, the speed of the actuation part during the actuation of each of the applicators was measured using a laser displacement gauge (produced by Keyence Corporation; LK-H150). Results of the measurement are shown in FIG. 35. The (a) of FIG. 35 shows implementation conditions and results of each of Examples 1 and 2, and the comparative example. The (b) of FIG. 35 shows the results of each of Examples 1 and 2, and the comparative example as a bar graph. As shown in FIG. 35, Example 1 could achieve a high transfer rate as compared with the comparative example, and improvement in puncture performance was found. In addition, as shown in FIG. 35, Example 2 could achieve a higher transfer rate as compared with Example 1, and further improvement in puncture performance was found.

Figure 36:
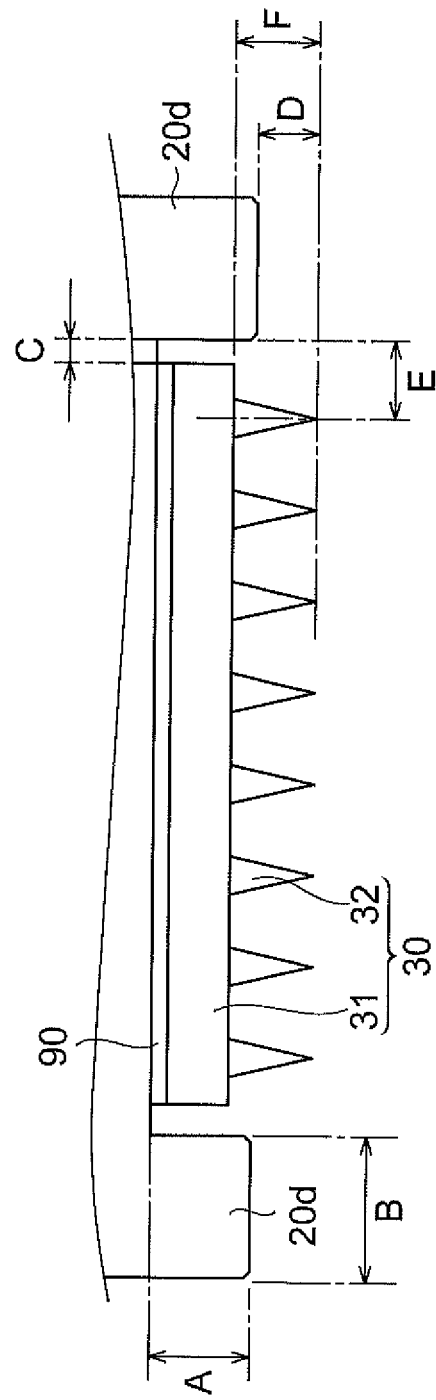
FIG. 36 schematically shows a part of the piston and the microneedle array in the examples.

Subsequently, influence of the protrusion parts on puncture performance was studied by performing an experiment while various parameters related to the protrusion parts $20d_1$ to $20d_4$ in the above-mentioned embodiments were changed. As shown in FIG. 36, the parameters include a height A of the protrusion part, a width B of the protrusion part, a distance (width of the recessed part) C between the protrusion part and the substrate of the microneedle array, a difference D in height between the leading end surface of the protrusion part and the leading end of the microneedle, a distance E between a central axis of a microneedle located outermost and the protrusion part, and an average length F of the microneedles. In FIG. 36, a reference sign $20d$ designates one or more protrusion parts, and reference signs 30, 31, and 32 designate the microneedle array, the substrate, and the microneedle, respectively, as well as a reference sign 90 designates an adhesive layer. The height A is a distance between a surface of the piston plate, on which the microneedle array is placed, and a leading end surface of the protrusion part. The width B is a length of the protrusion part along a radial direction of the piston. The distance C is a length between a side surface of the protrusion part and a side surface of the substrate. The difference D in height is acquired by using an average value because a height of an individual microneedle is not always the completely identical.

[Verification 1]

Figure 37:
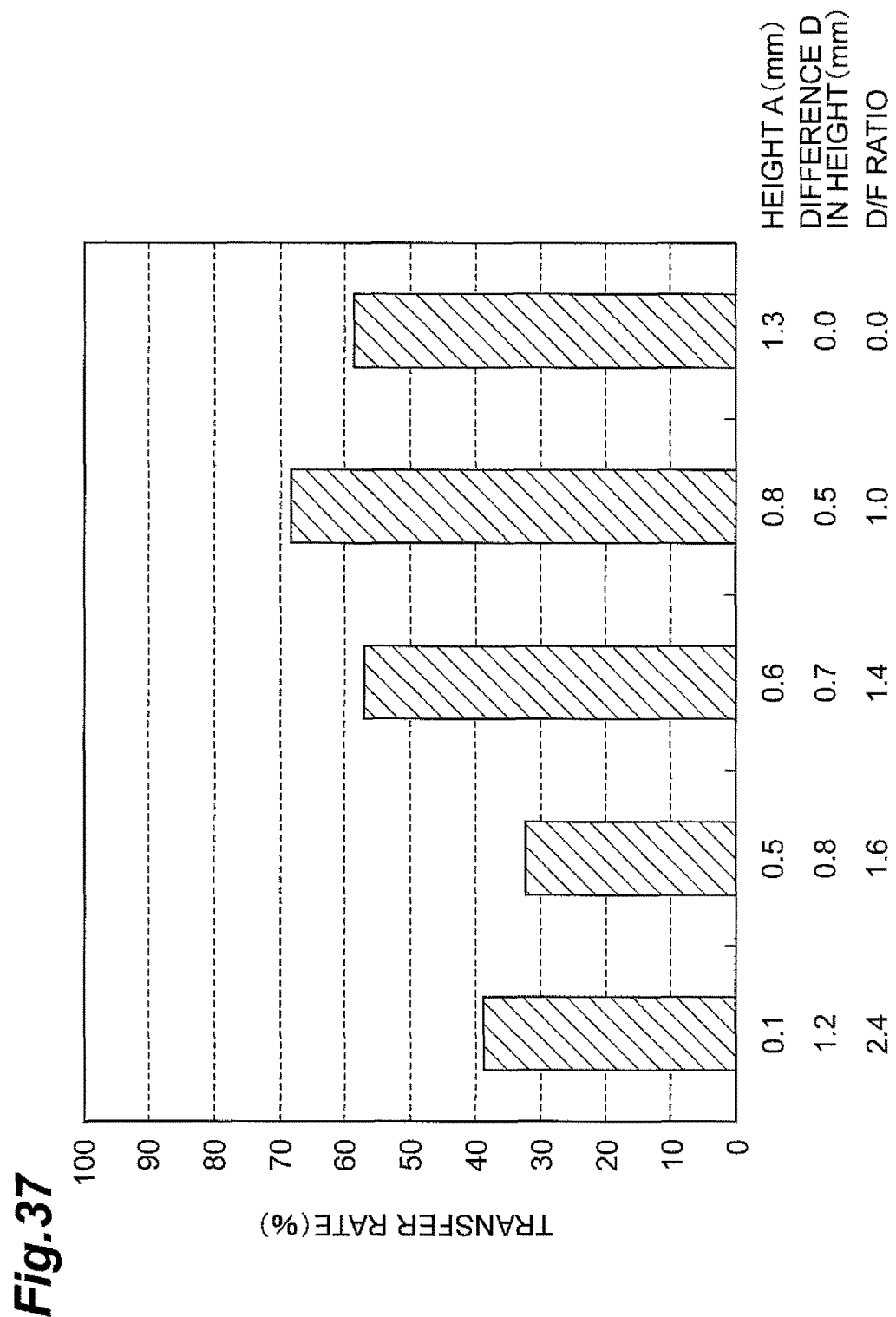
FIG. 37 is a graph showing results of the examples.

FIG. 37 is a graph showing relationships between the height A, the difference D in height, and the D/F ratio, and a transfer rate (%) of active ingredients into skin of a hairless rat, the relationships being acquired under the following conditions: the average length F of the microneedles was 0.5 mm; a thickness of the substrate was 0.7 mm; a thickness of the adhesive layer was 0.1 mm; fluorescein was used as the active ingredients; an application time of the microneedle array was five minutes; the width B was 0.7 mm; the distance C was 0.55 mm; and the distance E was 1.55 mm. According to this verification, it was found that the puncture performance tended to be improved if the height A was 0.6 mm or more (the difference D in height is 0.7 mm or less). It was also found that good puncture performance could be acquired if the difference D in height is 0 mm.

Locations of the active ingredients after administration at each height A were observed with a fluorescent microscope. Specifically, distribution of fluorescent light in a skin surface and distribution of the fluorescent light in a depth direction of the skin were observed. Results of the observations are shown in Table 1.

TABLE 1

| Height A (mm) | Distribution of fluorescent light in skin surface | Distribution of fluorescent light in depth direction of skin |
|---|---|---|
| 0.1 | Fluorescent light was found in region less than 30% of skin surface, and was not found in other regions. | Fluorescent light was found brighter at shallow depths of skin, and found darker at deep depths of skin. |
| 0.5 | Fluorescent light was found in region less than 30% of skin surface, and was not found in other regions. | Fluorescent light was found brighter at shallow depths of skin, and found darker at deep depths of skin. |
| 0.6 | Fluorescent light was found in region equal to or more than 50% of skin surface, and was not found in other regions. | Fluorescent light was found little at shallow depths of skin, and found bright at deep depths of skin. |
| 0.8 | Fluorescent light was found in region equal to or more than 50% of skin surface, and was not found in other regions. | Fluorescent light was found little at shallow depths of skin, and found bright at deep depths of skin. |
| 1.3 | Fluorescent light was found in region not less than 30% and less than 50% of skin surface, and was not found in other regions. | Fluorescent light was found brighter at shallow depths of skin, and found darker at deep depths of skin. |

[Verification 2]

Figure 38:
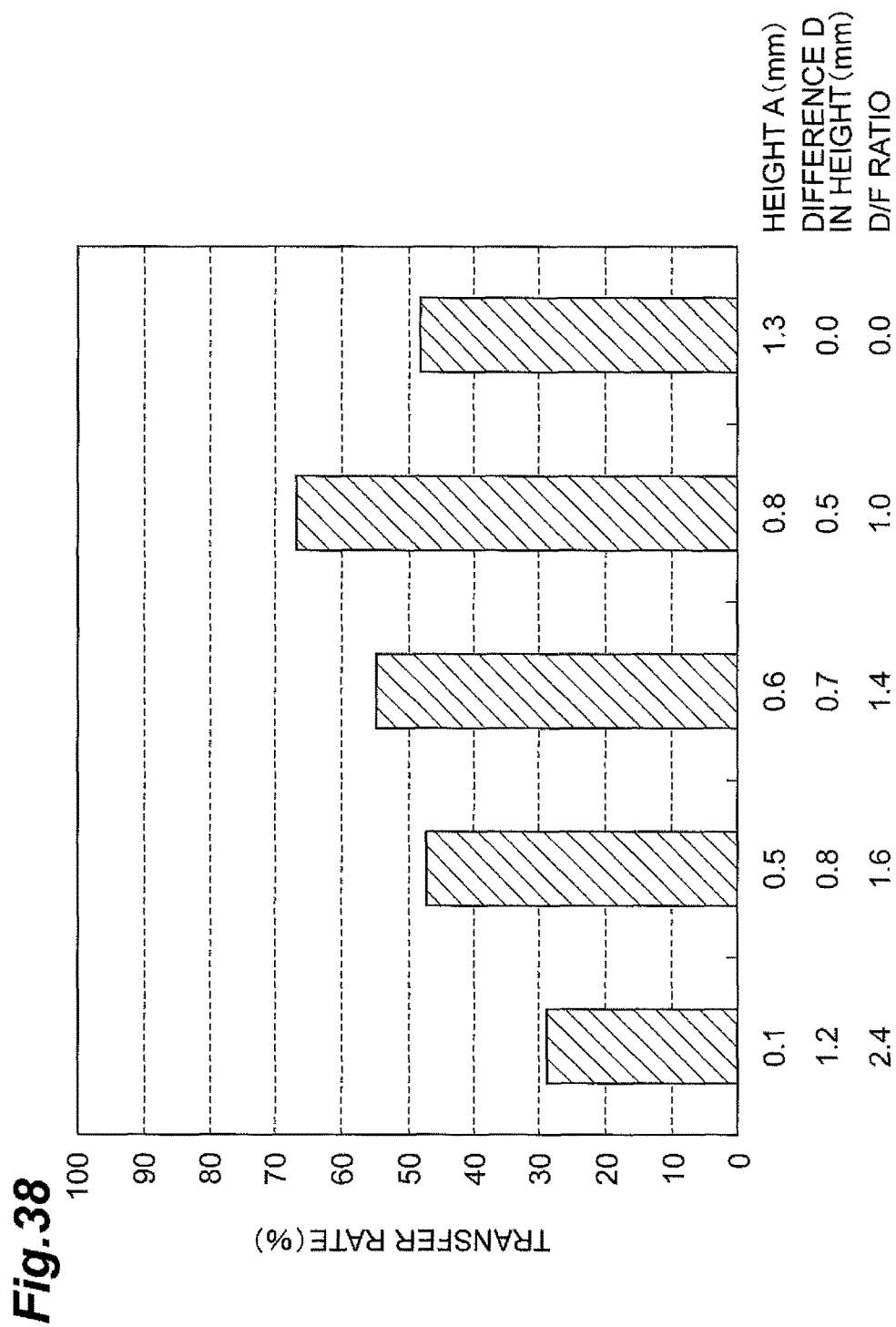
FIG. 38 is a graph showing results of the examples.

FIG. 38 is a graph showing relationships between the height A, the difference D in height, and the D/F ratio, and a transfer rate (%) of active ingredients into human skin, the relationships being acquired under the following conditions: the average length F of the microneedles was 0.5 mm; a thickness of the substrate was 0.7 mm; a thickness of the adhesive layer was 0.1 mm; OVA and Red No. 40 were used as the active ingredients; an application time of the microneedle array was five minutes; the width B was 2.09 mm; the distance C was 0.55 mm; and the distance E was 1.55 mm. According to this verification, it was found that a correlation between the height A and the puncture performance was verified, as with FIG. 37, even if the active ingredients and an object to be administered were changed.

[Verification 3]

Figure 39:
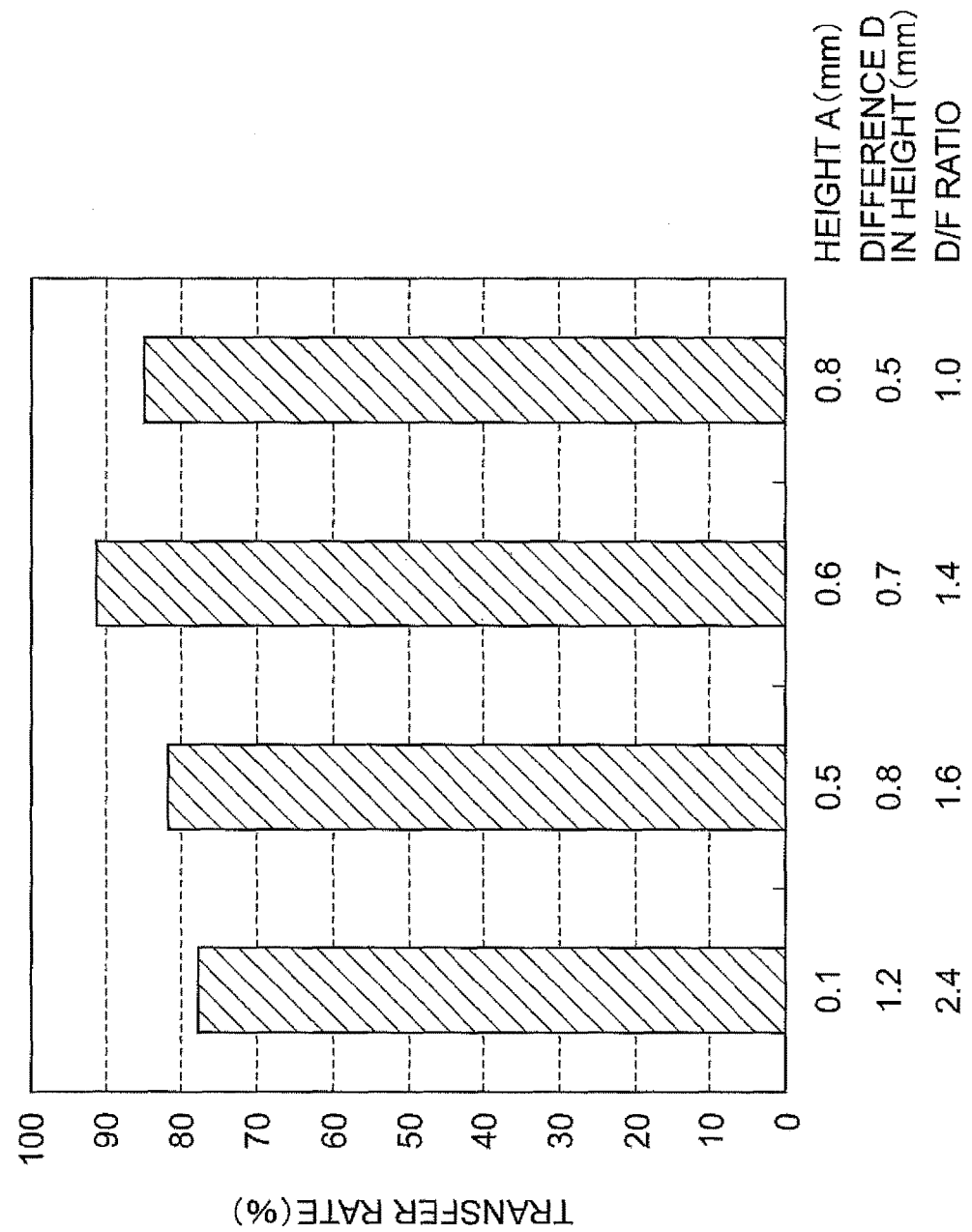
FIG. 39 is a graph showing results of the examples.

FIG. 39 is a graph showing relationships between the height A, the difference D in height, and the D/F ratio, and a transfer rate (%) of active ingredients into skin of a hairless rat, the relationships being acquired under the following conditions: the average length F of the microneedles was 0.5 mm; a thickness of the substrate was 0.7 mm; a thickness of the adhesive layer was 0.1 mm; fluorescein was used as the active ingredients; an application time of the microneedle array was five minutes; the width B was 2.09 mm; the distance C was 0.55 mm; and the distance E was 1.55 mm. According to this verification, it was found that a correlation between the height A and the puncture performance was verified, as with FIG. 37, even if the width B was changed.

Locations of the active ingredients after administration at each height A (distribution of fluorescent light in a skin surface and distribution of the fluorescent light in a depth direction of the skin) were observed with a fluorescent microscope. Results of the observations are shown in Table 2.

TABLE 2

| Height A (mm) | Distribution of fluorescent light in skin surface | Distribution of fluorescent light in depth direction of skin |
| --- | --- | --- |
| 0.1 | Fluorescent light was found in region less than 90% of skin surface, and was not found in other regions. | Fluorescent light was found brighter at shallow depths of skin, and found darker at deep depths of skin. |
| 0.5 | Fluorescent light was found in region not less than 90% and less than 95% of skin surface, and was not found in other regions. | Fluorescent light was found brighter at shallow depths of skin, and found darker at deep depths of skin. |
| 0.6 | Fluorescent light was found in region equal to or more than 95% of skin surface, and was not found in other regions. | Fluorescent light was found little at shallow depths of skin, and found bright at deep depths of skin. |
| 0.8 | Fluorescent light was found in region equal to or more than 95% of skin surface, and was not found in other regions. | Fluorescent light was found little at shallow depths of skin, and found bright at deep depths of skin. |
| 1.3 | Fluorescent light was found in region less than 90% of skin surface, and was not found in other regions. | Fluorescent light was found brighter at shallow depths of skin, and found darker at deep depths of skin. |

[Verification 4]

Transfer rates of active ingredients were measured under the following conditions: the average length F of the microneedles was 0.5 mm; a thickness of the substrate was 0.7 mm; a thickness of the adhesive layer was 0.1 mm; fluorescein was used as the active ingredients; the microneedle array was applied to skin of a hairless rat for five minutes; the width B was 0.7 mm; the distance C was 0.55 mm; the distance E was 1.55 mm; and the height A (and the difference D in height) was 0.1 mm (1.2 mm), and 0.6 mm (0.7 mm). As a result, the transfer rate was 49.4% when the height A was 0.1 mm (the difference D in height was 1.2 mm), and was 88.9% when the height A was 0.6 mm (the difference D in height was 0.7 mm). When locations of the active ingredients after administration were observed with a fluorescent microscope, it was found that punctures were uneven under conditions where the height A was 0.1 mm (the difference D in height was 1.2 mm) as well as the active ingredients remained on a surface of the skin. In contrast, punctures were uniform when the height A was 0.6 mm (the difference D in height was 0.7 mm) as well as little amount of the active ingredients remained on the surface of the skin. As a result, it was found that appropriate selection of the height A (or the difference D in height) improved uniformity of the punctures and the transfer rate.

[Verification 5]

Figure 40:
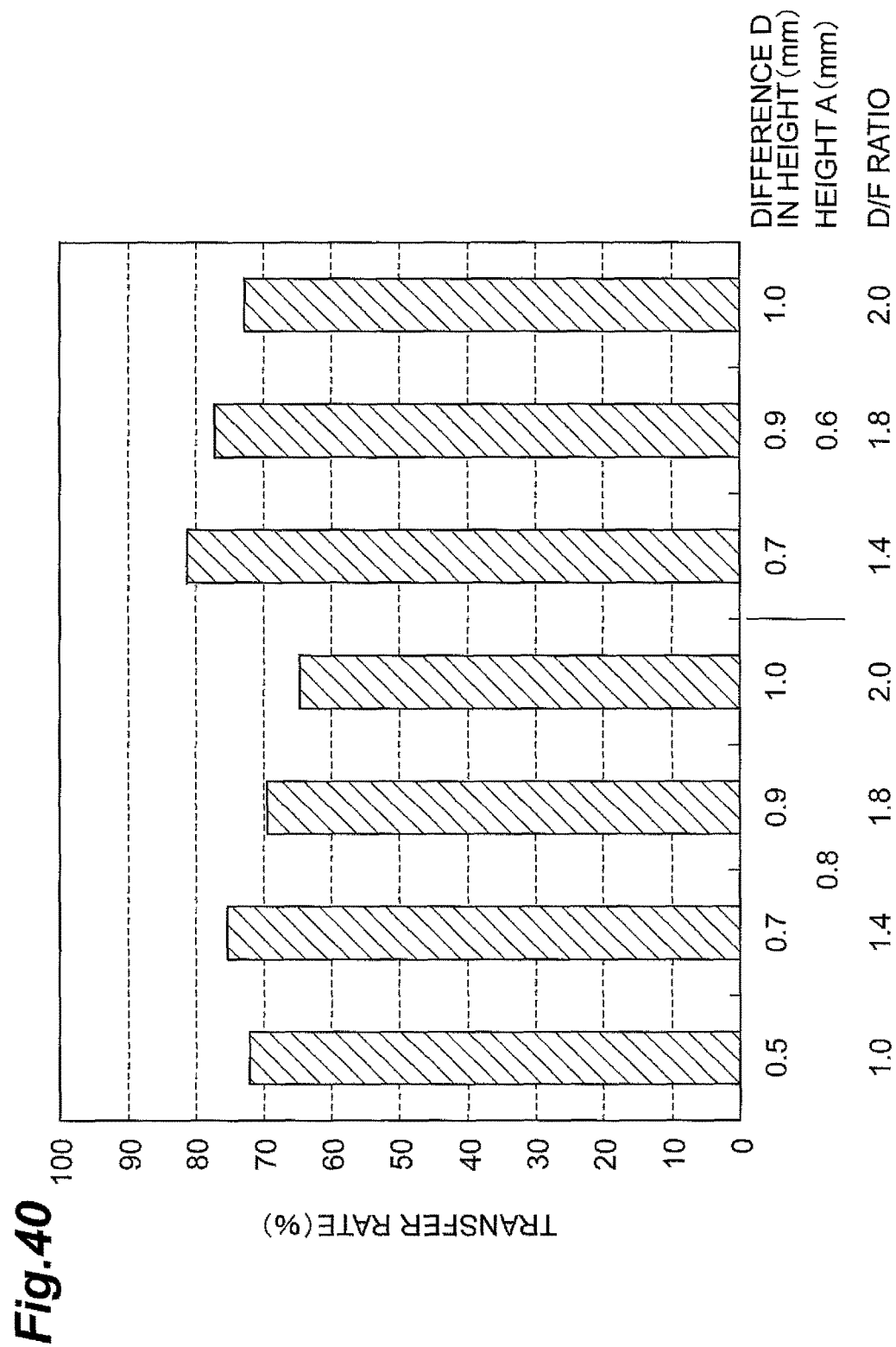
FIG. 40 is a graph showing results of the examples.

FIG. 40 is a graph showing relationships between the height A, the difference D in height, and the D/F ratio, and a transfer rate (%) of active ingredients into human skin, the relationships being acquired under the following conditions: the average length F of the microneedles was 0.5 mm; a thickness of the substrate was 0.7 mm; lidocaine was used as the active ingredients; an application time of the microneedle array was five minutes; the width B was 2.09 mm; the distance C was 0.55 mm; and the distance E was 1.55 mm; the height A was set at 0.6 mm or 0.8 mm; and the difference D in height was adjusted by changing the thickness of the adhesive layer. According to this verification, it was suggested that the difference D in height was important to improve the puncture performance.

[Verification 6]

Figure 41:
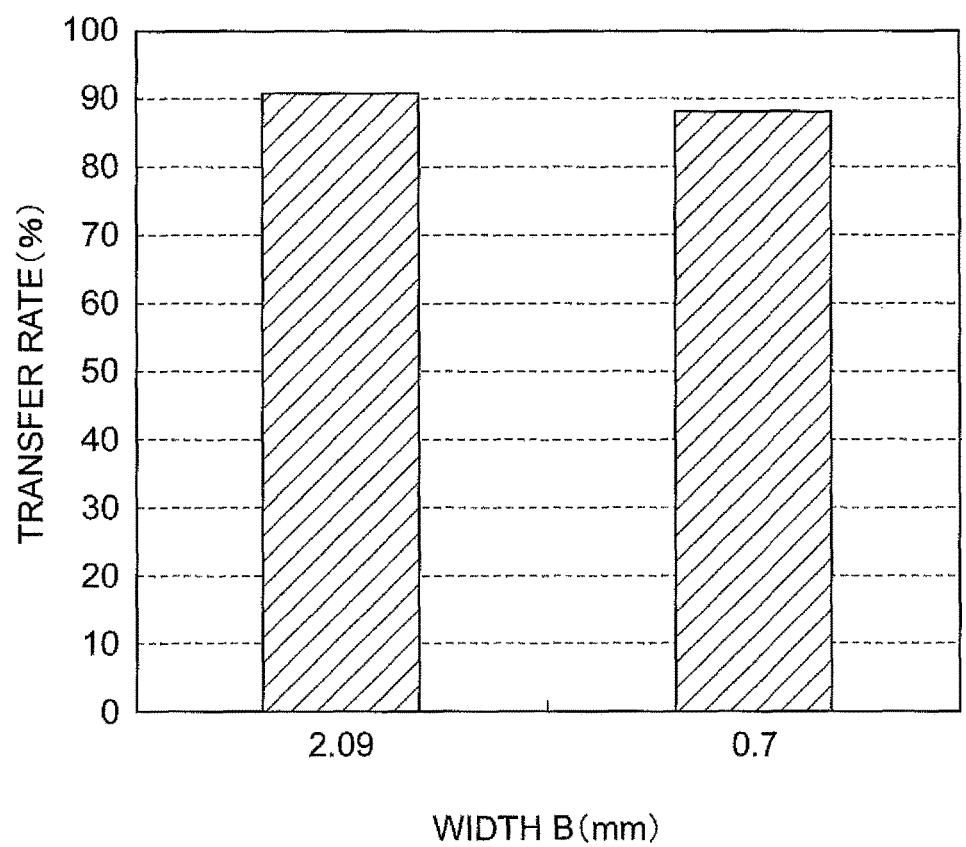
FIG. 41 is a graph showing results of the examples.

FIG. 41 is a graph showing relationships between the width B and the transfer rate (%) of active ingredients into skin of a hairless rat, the relationships being acquired under the following conditions: the average length F of the microneedles was 0.5 mm; a thickness of the substrate was 0.7 mm; a thickness of the adhesive layer was 0.1 mm; fluorescein was used as the active ingredients; an application time of the microneedle array was five minutes; the height A was 0.6 mm; the distance C was 0.55 mm; the difference D in height was 0.7 mm; the distance E was 1.55 mm; and the width B was set at 2.09 mm and 0.7 mm. According to this verification, it was found that the width B did not affect the puncture performance.

[Verification 7]

Figure 42:
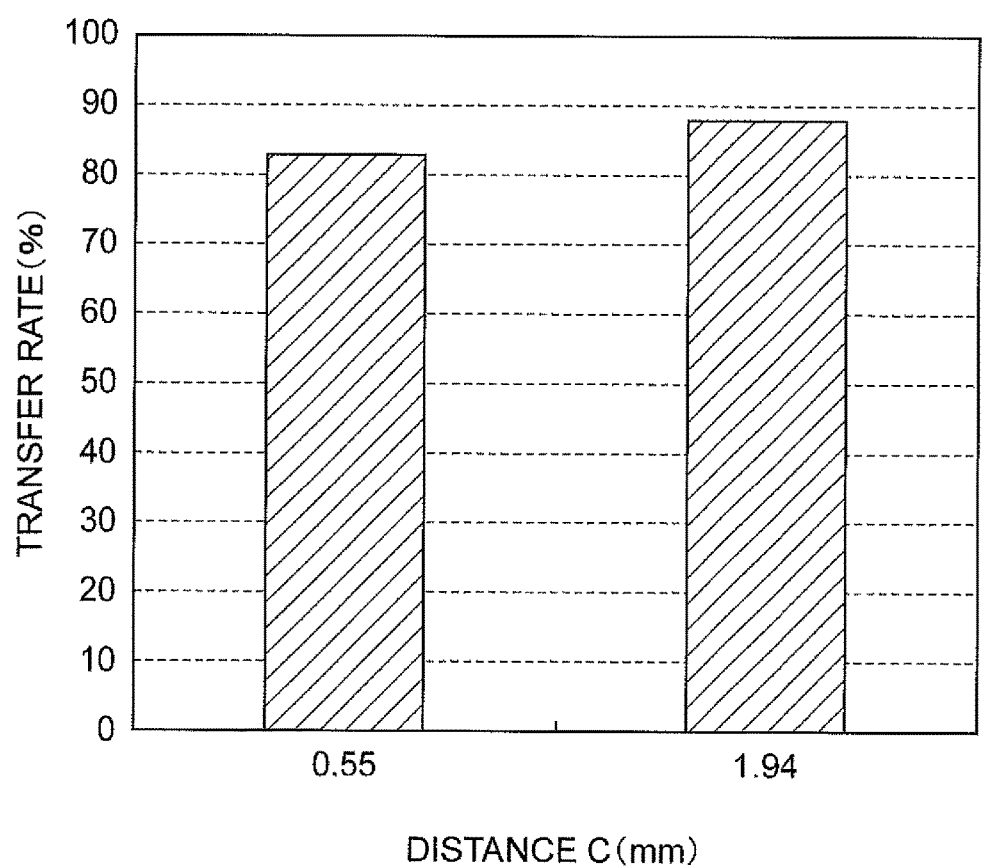
FIG. 42 is a graph showing results of the examples.

FIG. 42 is a graph showing relationships between the distance C and the transfer rate (%) of active ingredients into skin of a hairless rat, the relationships being acquired under the following conditions: the average length F of the microneedles was 0.5 mm; a thickness of the substrate was 0.7 mm; a thickness of the adhesive layer was 0.1 mm; fluorescein was used as the active ingredients; an application time of the microneedle array was five minutes; the height A was 0.6 mm; the width B was 0.7 mm; the difference D in height was 0.7 mm; the distance C was set at 0.55 mm and 1.94 mm; and the distance E was set at 1.55 mm and 2.94 mm. According to this verification, it was found that the distance C did not affect the puncture performance. In addition, a distance between a sidewall of the casing and the protrusion part (a sum of this distance and the distance C is constant because the width B is fixed) also did not affect the puncture performance.

Accordingly, the present invention can be defined as follows.

(Item 1)

An applicator configured to transfer an active ingredient into a body through skin by a puncture in the skin with microneedles, the applicator comprising a piston plate that is provided on its one main surface with a first protrusion part and at least one second protrusion part, the first protrusion part being provided on its surface with the microneedles, and the second protrusion part being provided in a periphery of the first protrusion part while spaced apart from the first protrusion part.

(Item 2)

In the applicator described in Item 1, an adhesive substance with adhesive capability is provided in at least a part of a surface of the second protrusion part.

(Item 3)

In the applicator described in Item 1 or 2, a plurality of the second protrusion parts are provided on the piston plate, the plurality of the second protrusion parts being disposed in such a way as to surround the first protrusion part.

(Item 4)

In the applicator described in Item 1 or 2, the second protrusion part has an annular shape surrounding the entire periphery of the first protrusion part.

(Item 5)

In the applicator described in any one of Items 1 to 4, a portion between the first protrusion part and the second protrusion part forms a recessed part recessed from surfaces of the protrusion parts.

(Item 6)

An applicator configured to transfer an active ingredient into a body through skin by a puncture in the skin with microneedles, the applicator comprising a piston plate that transmits impact force to a microneedle array in which the microneedles are provided in a predetermined region when one main surface of the piston plate collides against the microneedle array, the piston plate including at least one protrusion part that is provided in the one main surface in such a way as to surround the microneedle array while spaced apart from the predetermined region of the microneedle array.

(Item 7) In the applicator described in Item 6, an adhesive substance with adhesive capability is provided in at least a part of a surface of the protrusion part.

(Item 8)

In the applicator described in Item 6 or 7, a plurality of the protrusion parts are provided on the piston plate, the plurality of the protrusion parts being disposed in such a way as to surround the microneedle array.

(Item 9)

In the applicator described in Item 6 or 7, the protrusion part has an annular shape surrounding the entire periphery of the microneedle array.

(Item 10)

In the applicator described in any one of Items 6 to 9, a portion between the predetermined region in the microneedle array and the protrusion part forms a recessed part recessed from the predetermined region and a surface of the protrusion part.

REFERENCE SIGNS LIST

10 . . . casing
12 . . . main body part
14 . . . cover part
20 . . . piston plate
$20d_1$ to $20d_4$ . . . protrusion part
22 . . . recessed part
30, 30A . . . microneedle array
32 . . . microneedle
35 . . . recessed part
40 . . . conical coil spring
50 . . . release member
60 . . . adhesive substance
A . . . applicator

The invention claimed is:

1. An applicator configured to transfer an active ingredient into a body through skin by a puncture in the skin with microneedles, the applicator comprising:
   a casing;
   a piston plate housed in a main body part of the casing and movable in a top-bottom direction inside of the main body part, wherein
   the piston plate comprises a lower surface including:
   a microneedle region where a first protrusion part is located, the microneedles being provided in the first protrusion part;
   at least one second protrusion part provided in a periphery of the microneedle region; and
   a recessed part formed between the first protrusion part and the at least one second protrusion part, and recessed from both of a surface of the first protrusion part and a surface of each of the at least one second protrusion parts, wherein
   a plurality of the second protrusion parts are provided on the piston plate, and
   the plurality of the second protrusion parts being disposed in such a way as to surround the first protrusion part.

2. The applicator according to claim 1, wherein
   an adhesive substance with adhesive capability is provided in at least a part of the surface of the second protrusion part.

3. The applicator according to claim 1, wherein
   a difference in height between a leading end surface of the at least one second protrusion part and a leading end of the microneedle protruding outward from the leading end surface is 0 mm or more.

4. The applicator according to claim 3, wherein
   the difference in height is 0 to 1.0 mm.

5. The applicator according to claim 3, wherein
   a value D/F is not less than 0.0 and not more than 1.4, where D is the difference in height, and F is an average length of the microneedles.

6. The applicator according to claim 5, wherein
   the value D/F is not less than 1.0 and not more than 1.4.

7. An applicator configured to transfer an active ingredient into a body through skin by a puncture in the skin with microneedles, the applicator comprising:
   a casing;
   a piston plate housed in a main body part of the casing and movable in a top-bottom direction inside of the main body part, wherein
   the piston plate comprises a lower surface that transmits impact force to a microneedle array in which the microneedles are provided in a predetermined region by colliding against the microneedle array,
   at least one protrusion part that is provided in the lower surface of the piston plate in such a way as to surround the microneedle array while spaced apart from the predetermined region of the microneedle array, and
   a portion between the predetermined region of the microneedle array and the at least one protrusion part forms a recessed part recessed from both of a surface of the predetermined region and a surface of each of the at least one protrusion parts, wherein a plurality of the protrusion parts are provided on the piston plate, and the plurality of the protrusion parts are disposed in such a way as to surround the microneedle array.

8. The applicator according to claim 7, wherein an adhesive substance with adhesive capability is provided in at least a part of the surface of the protrusion part.

\* \* \* \* \*